(12) United States Patent
Saadat et al.

(10) Patent No.: US 6,939,313 B2
(45) Date of Patent: Sep. 6, 2005

(54) DEVICE FOR SENSING PARAMETERS OF A HOLLOW BODY ORGAN

(76) Inventors: Vahid Saadat, 12679 Kane Dr., Saratoga, CA (US) 95070; Ross Tsugita, 1653 Gretel La., Mountain View, CA (US) 94040-3706

( * ) Notice: Subject to any disclaimer, the term of this patent is extended or adjusted under 35 U.S.C. 154(b) by 281 days.

(21) Appl. No.: 10/146,014

(22) Filed: May 14, 2002

(65) Prior Publication Data

US 2003/0088187 A1 May 8, 2003

Related U.S. Application Data

(63) Continuation-in-part of application No. 09/904,212, filed on Jul. 12, 2001, now abandoned.

(51) Int. Cl.[7] .......................... A61B 5/103; A61B 5/117
(52) U.S. Cl. ..................................................... 600/587
(58) Field of Search ................................ 600/585, 433, 600/434, 435, 474, 481, 505, 549, 1; 374/141, 148, 166, 179; 606/41, 194, 32, 49; 604/530, 913, 95.01; 607/122, 99; 378/44

(56) References Cited

U.S. PATENT DOCUMENTS

| | | |
|---|---|---|
| 4,215,275 A | 7/1980 | Wickersheim |
| 4,301,023 A | 11/1981 | Schuberth et al. |
| RE32,204 E | 7/1986 | Halvorsen |
| 4,699,147 A | 10/1987 | Chilson et al. |
| 4,777,955 A | 10/1988 | Brayton et al. |
| 4,862,887 A | 9/1989 | Weber et al. |
| 4,883,459 A | 11/1989 | Calderon |
| 4,884,573 A * | 12/1989 | Wijay et al. ................ 606/194 |
| 4,952,033 A | 8/1990 | Davis |
| 4,958,642 A | 9/1990 | Christian et al. |
| 4,995,398 A | 2/1991 | Turnidge |

(Continued)

FOREIGN PATENT DOCUMENTS

| | | |
|---|---|---|
| WO | WO 97/10748 A1 | 3/1997 |
| WO | WO 01/13603 A1 | 3/2000 |
| WO | WO 00/27278 A1 | 5/2000 |
| WO | WO 01/74263 A1 | 10/2001 |

OTHER PUBLICATIONS

Pasterkamp, G. et al. (Jul. 2000). "Techniques Characterizing the Coronary Atherosclerotic Plaque: Influence on Clinical Decision Making?" *J. Am. Coll. Cardiol.* 36(1):13–21.
Stefanadis, C. et al. (Apr. 1999). "Thermal Heterogeneity Within Human Atherosclerotic Coronary Arteries Detected In Vivo," *Circulation* 99:1965–1971.
Bolz, Ray E. and Tuve, George L. (eds) (1973) Chapter 10 Transducers and Measurement Techniquest, *CRC Handbook of Tables for Applied Engineering Science*, 2nd edition, CRC Press, pp. 975–978.
Brochure from Parker (May 1992) Compumotor Digiplan, Positioning Control Systems and Drives, Parker, Catalog 8000, Engineering Reference and Application Solutions, Table of Contents and A77 A80 (Glossary of Terms).
Inflammation Hypothesis, Vulnerable Plaque, Milestons in Vulnerable Plaque and Atherosclerosis Research, located at <http://www.vp.org/Milestones/Milestones.htm> visited on Jun. 30, 2002, 2 pages, see under # 1856.

*Primary Examiner*—Max F. Hindenburg
*Assistant Examiner*—Brian Szmal

(57) ABSTRACT

A device for sensing the profile of a hollow body organ includes a hollow guidewire or probe carrying a sensor. The hollow probe includes a distal coiled end tube with a tip bent at an angle between about 10° to 90° relative to the probe longitudinal axis and having a torque response of no more than about 0.4 ozf in. The flexural rigidity of the distal end tube relative to the mid and proximal end tubes forming the probe is generally in the range of about 1:(4 to 4,400):(110 to 13,000), respectively. An actuator is detachably secured to the probe and includes one or several motors which allow the sensor to travel in a rotational and axial path through the body organ.

45 Claims, 27 Drawing Sheets

U.S. PATENT DOCUMENTS

| | | |
|---|---|---|
| 5,054,501 A | 10/1991 | Chuttani et al. |
| 5,069,226 A | 12/1991 | Yamauchi et al. |
| 5,124,819 A | 6/1992 | Davis |
| 5,178,159 A | 1/1993 | Christian |
| 5,237,996 A | 8/1993 | Waldman et al. |
| 5,279,299 A | 1/1994 | Imran |
| 5,304,194 A | 4/1994 | Chee et al. |
| 5,342,300 A | 8/1994 | Stefanadis et al. |
| 5,623,940 A | 4/1997 | Daikuzono |
| 5,657,764 A | 8/1997 | Coulter et al. |
| RE35,648 E | 11/1997 | Tenerz et al. |
| 5,701,905 A | 12/1997 | Esch |
| 5,730,741 A | 3/1998 | Horzewski et al. |
| 5,733,739 A | 3/1998 | Zakim et al. |
| 5,741,214 A | 4/1998 | Ouchi et al. |
| 5,769,846 A | 6/1998 | Edwards et al. |
| 5,771,895 A | 6/1998 | Slager |
| 5,782,741 A | 7/1998 | Bradshaw et al. |
| 5,871,449 A | 2/1999 | Brown |
| 5,910,101 A | 6/1999 | Andrews et al. |
| 5,924,997 A | 7/1999 | Campbell |
| 5,935,075 A | 8/1999 | Casscells et al. |
| 5,938,624 A | 8/1999 | Akerfeldt et al. |
| 5,980,563 A | 11/1999 | Tu et al. |
| 5,989,242 A | 11/1999 | Saadat et al. |
| 6,010,476 A | 1/2000 | Saadat |
| 6,071,277 A | 6/2000 | Farley et al. |
| 6,090,052 A | 7/2000 | Akerfeldt et al. |
| 6,106,486 A | 8/2000 | Tenerz et al. |
| 6,142,958 A | 11/2000 | Hammarström et al. |
| 6,156,046 A | 12/2000 | Passafaro et al. |
| 6,167,763 B1 | 1/2001 | Tenerz et al. |
| 6,196,980 B1 | 3/2001 | Akerfeldt et al. |
| 6,197,021 B1 | 3/2001 | Panescu et al. |
| 6,245,026 B1 | 6/2001 | Campbell et al. |
| 6,267,746 B1 | 7/2001 | Bumbalough |
| 6,267,781 B1 | 7/2001 | Tu |
| 6,312,425 B1 | 11/2001 | Simpson et al. |
| 6,371,928 B1 | 4/2002 | Mcfann et al. |
| 6,406,442 B1 | 6/2002 | McFann et al. |
| 6,786,905 B2 * | 9/2004 | Swanson et al. ............... 606/32 |
| 2001/0053882 A1 | 12/2001 | Haddock et al. |
| 2002/0067754 A1 | 6/2002 | Werneth |
| 2003/0055307 A1 * | 3/2003 | Elmaleh et al. ................. 600/1 |

\* cited by examiner

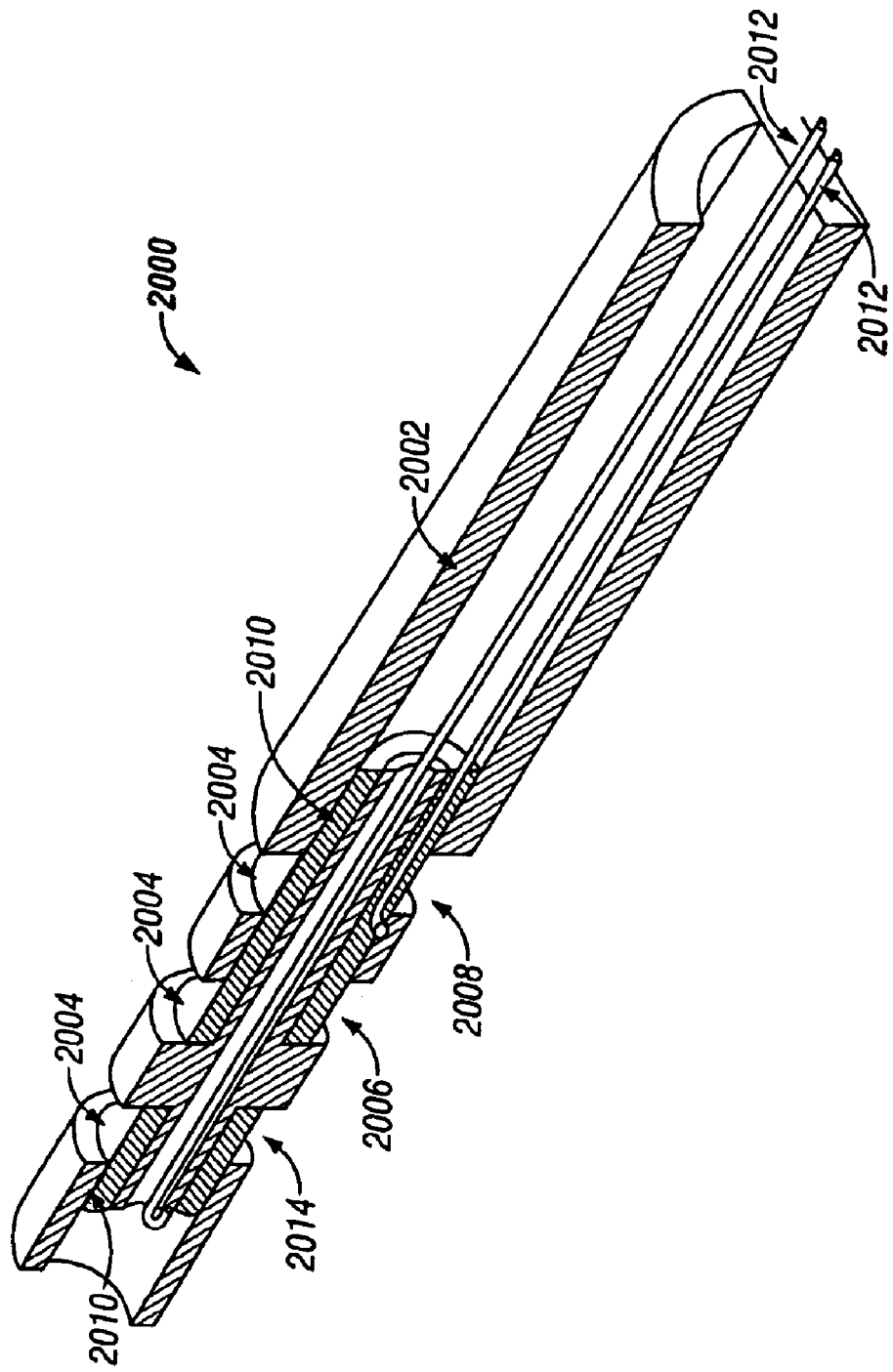

DEVICE FOR SENSING PARAMETERS OF A HOLLOW BODY ORGAN

CROSS-REFERENCE TO RELATED APPLICATIONS

This application is a continuation-in-part of U.S. patent application Ser. No. 09/904,212, filed on Jul. 12, 2001 (now abandoned).

TECHNICAL FIELD OF THE INVENTION

This invention relates generally to invasive medical devices and more particularly to devices for sensing the profile of the interior wall of a hollow body organ such as a blood vessel.

BACKGROUND OF THE INVENTION

Acute ischemic syndromes involving arterial blood vessels, such as myocardial infarction, or heart attack, and stroke, frequently occur when atherosclerotic plaque ruptures, triggering the formation of blood clots, or thrombosis. Plaque that is inflamed is particularly unstable and vulnerable to disruption, with potentially devastating consequences. Therefore, there is a strong need to detect and locate this type of plaque so that treatment can be initiated before the plaque undergoes disruption and induces subsequent life-threatening clotting.

Various procedures are known for detecting and locating plaque in a blood vessel. Angiography is one such procedure in which X-ray images of blood vessels are generated after a radio-opaque dye is injected into the blood stream. This procedure is capable of locating plaque in an artery, but is not capable of revealing whether the plaque is the inflamed, unstable type.

Researchers, acting on the theory that inflammation is a factor in the development of atherosclerosis, have discovered that local variations of temperature along arterial walls can indicate the presence of inflamed plaque. The temperature at the site of inflammation, i.e., the unstable plaque, is elevated relative to adjacent plaque-free arterial walls.

Using a tiny thermal sensor at the end of a catheter, the temperature at multiple locations along an arterial wall were measured in people with and without atherosclerotic arteries. In people free of heart disease, the temperature was substantially homogeneous wherever measured: an average of 0.65 degrees F. above the oral temperature. In people with stable angina, the temperature of their plaques averaged 0.19 degrees F. above the temperature of their unaffected artery walls. The average temperature increase in people with unstable angina was 1.23 degrees F. The increase was 2.65 degrees F. in people who had just suffered a heart attack. Furthermore, temperature variation at different points at the plaque site itself was found to be greatest in people who had just had a heart attack. There was progressively less variation in people with unstable angina and stable angina.

The temperature heterogeneity discussed above can be exploited to detect and locate inflamed, unstable plaque through the use of cavity wall profiling apparatus. Typically, cavity wall profiling apparatus are comprised of temperature indicating probes such as thermocouples, thermistors, fluorescence lifetime measurement systems, resistance thermal devices and infrared measurement devices.

One problem with conventional cavity wall profiling apparatus is that they usually exert an undue amount of force on the region of interest. If the region of interest cannot withstand these forces, it may be damaged. The inside walls of a healthy human artery are vulnerable to such damage. Furthermore, if inflamed, unstable plaque is present it may be ruptured by such forces.

Another problem with conventional cavity wall profiling apparatus is that they can only measure the temperature at one specific location. In order to generate a map of the cavity temperature variation, one would need to move the temperature indicating probe from location to location. This can be very tedious, can increase the risk of damaging the vessel wall or rupturing vulnerable plaque, and may not resolve temporal characteristics of the profile with sufficient resolution. An array of probes could be employed but that could be very big and heavy.

BRIEF SUMMARY OF THE INVENTION

According to one aspect of the invention, a device is provided for sensing the temperature profile of a hollow body organ. The device includes a hollow guidewire, a temperature sensor disposed on or within the guidewire, and an optional catheter through which the guidewire may be delivered. The guidewire has a relaxed configuration externally of the catheter that is formed to provide contact with the wall of the hollow body organ. The guidewire also has a contracted configuration internally of the catheter and is of a lesser diameter than the catheter.

According to another aspect of the invention, the device is used by contracting the guidewire elastically and constraining the guidewire within the catheter. The catheter and guidewire are advanced to a region of interest in a hollow body organ. The catheter is withdrawn to expose the distal portion of the guidewire which may then reconfigure into a relaxed configuration to make contact with the hollow body organ. Alternatively, the catheter may be held stationary relative to the hollow body organ and the guidewire may be advanced until the distal portion of the guidewire is exposed to reconfigure. The guidewire is moved longitudinally and rotated, continuously or continually, to sense the temperature of the hollow body organ at multiple locations.

Alternatively, the catheter may be omitted entirely from the deployment procedure. Rather than using a catheter or sheath to restrain the distal portion of the guidewire during deployment, the guidewire may simply be inserted and advanced within the hollow body organ to the tissue region of interest while in its relaxed configuration. For instance, an introducer and/or guide catheter may be positioned percutaneously through the skin into the body of a patient and the guidewire may simply be inserted without the use of a separate catheter directly into, e.g., the vasculature, via the introducer. During insertion, the guidewire may be inserted into the body while the probe is in its relaxed configuration. Except when initially introduced or withdrawn through the introducer into the body, the probe may remain in its relaxed configuration.

In accordance with yet another aspect of the present invention, the probe or guidewire includes a hollow, flexible, elongate stem having proximal and mid portions and a distal end portion which terminates in a coil having at least a tip segment thereof biased away from the rotational axis of the probe at an angle between approximately 30° to 75° relative to the stem longitudinal axis, and more preferably between approximately 40° to 60°, and having a torque response of no more than about 0.4 ozf in. Moreover, a transducer is mounted to the coil, a connector is located at the proximal end portion of the stem, and at least one conductor connects the transducer to the connector. An elongate mandrel having a bent tip extends through the coil and provides the coil with its bent configuration.

The probe may be configured such that the coil rotates about the proximal end portion of the stem in response to the rotation of an actuation shaft extending through the proximal end portion of the stem. The proximal end portion of the stem can also define a sheath slidable on the actuation shaft and operably coupled to the coil for allowing the axial reciprocal movement of the coil. An actuator may surround the proximal end portion of the stem and be adapted to provide both rotational and axial or longitudinal movement to the stem to allow the sensor to travel in a helical path through the desired body organ.

Moreover, and depending upon the particular desired application, the materials and/or shapes of the proximal, mid and distal end portions of the stem may be varied to provide a flexural rigidity ratio between the coil and the mid portion and the proximal end portion in the range of about 1:(4 to 4,400):(110 to 13,000), respectively, and more preferably 1:400:1200, respectively.

To ensure contact between the probe and the vessel wall, various impedance measurement devices or sensors may also be provided in addition to the thermal sensors or transducers mounted in the tip segment.

The actuator which controls the rotational and axial movement of the probe may be constructed as a handle. The probe may be attached via an optionally removable chuck to the handle and both the chuck and the probe may be electrically connected to an amplifier positioned within the handle. The amplifier is preferably configured to rotate while maintaining electrical contact with the probe. Moreover, various motors under the control of a motor controller, are used to control both the rotational and axial movement of the probe. A processor, e.g., a computer, is used to not only track/control the positioning and movement of the probe, but is also used to process the signals acquired by the probe. During the measurement or scanning process, the rate and pitch at which the vessel walls are scanned may be automatically varied by the processor to increase the measured sampling resolution upon the determination of a threshold measurement value being exceeded.

While the processor and/or controller may be used to control the movement of the probe, an alternative embodiment may incorporate an intervening chuck and connector cable to allow for the manual manipulation of the probe. This embodiment utilizes a separate chuck which is used to receive the probe. The chuck may then be connected to the probe actuator via the connector cable. During normal operation, the intervening chuck and connector cable may remain attached to the probe actuator or they may be connected when manual manipulation is desired. To accomplish the manipulation, the physician or surgeon may simply rotate and/or axially move the probe via the intervening chuck while maintaining the sterility of the probe and probe actuator. Alternatively, the intervening chuck may be omitted altogether and the probe may simply be attached to a connector cable which is configured to directly receive the probe connector.

Further aspects and advantages of the present invention are apparent from the following description of the preferred embodiments referring to the drawings.

BRIEF DESCRIPTION OF THE DRAWINGS

In the drawings,

FIG. 25A is a cross-sectioned perspective view of a proximal end of a probe;

DETAILED DESCRIPTION OF THE INVENTION

Figure 1:
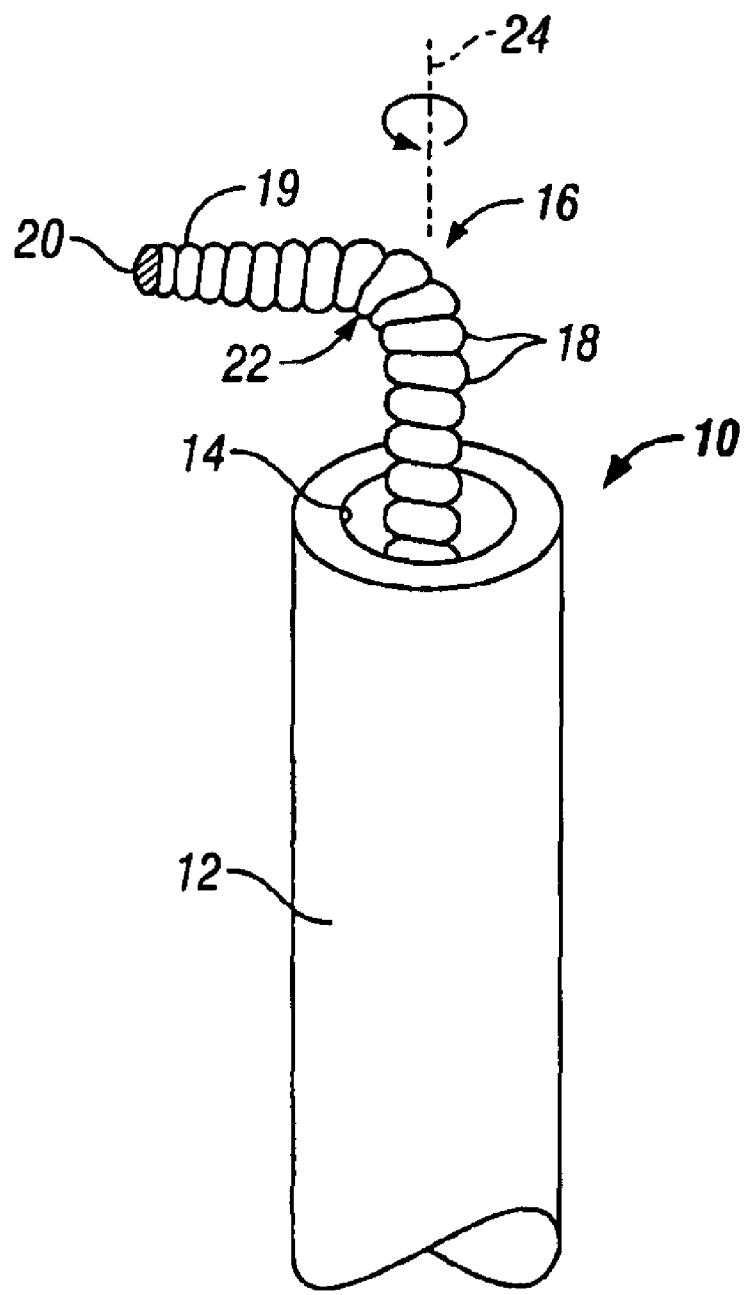
FIG. 1 is a perspective view of an embodiment of the present invention.

FIG. 1 shows a device 10 for profiling the wall of a hollow body organ. Device 10 includes a lumened catheter 12 having a central lumen 14, a hollow guidewire 16 that defines a conduit comprising a metal wire 18 or the like in the shape of a coil defining a central lumen (not shown), and a thermal sensor 20 disposed at the terminal end of the distal portion of guidewire 16. Conventional conductors or other signal carrying structures (not shown) are provided to convey signals from the thermal sensor 20 along guidewire 16 and out of the proximal portion of guidewire 16 for connection to appropriate signal processing apparatus that converts the signals to a temperature indication. Thermal sensor 20 can be, e.g., a thermocouple, a thermistor, an infrared radiation sensor, fiberoptic oxygen sensor, ultrasonic transducer, impedance sensor, pH sensor, mechanical force sensor (e.g., strain gauge), etc., for example, and is secured by appropriate mechanical or adhesive means to the terminal end of guidewire 16. Moreover, radio-opaque materials, e.g., platinum, gold, etc., may be formed in epoxy materials which may be used to attach sensor 20 to guidewire 16. Alternatively, one or several radio-opaque marker bands 19, preferably made of biocompatible materials such as those listed above, may be formed proximally of sensor 20 along guidewire 16 to assist in denoting the location of sensor 20 during a measurement procedure. Typical thermocouples which can be used may include T-type thermocouples (Copper and Constantan) having thermoelectric conversion coefficients of about 40.3 $\mu V/°C$.

Hollow guidewire 16 is made of thin wire 18 wound, for example around a mandrel, into small helical coils of desired diameter that lie tightly adjacent one another to form a hollow tube having a central passageway or lumen therethrough. Guidewire 16 may have an outer diameter which is uniform along its length; alternatively, the diameter may be varied, e.g., having diameter decrease proximally along the length of guidewire 16 or having sections of differing guidewire 16 diameters along the length. Guidewire 16 has an outer diameter somewhat less than the inner diameter of catheter 12 to permit guidewire 16 to slide freely within the lumen 14 of catheter 12. In addition, guidewire 16, in its relaxed configuration, is shaped in the form of a bend 22 at the distal portion thereof, the bend 22 being spaced from the terminal end of guidewire 16 at which thermal sensor 20 is disposed. Consequently, thermal sensor 20 is displaced radially from the longitudinal axis 24 of guidewire 16 and catheter 12 when guidewire 16 is in the relaxed, bent configuration. Through external manipulation, guidewire 16 in the relaxed, bent configuration can be made to rotate about axis 24, continuously or continually, depending on the response time for the sensor, thereby causing thermal sensor 20 to traverse a circumferential or helical path about axis 24 while providing temperature information. Guidewire 16 can be deformed elastically into a substantially straight configuration, i.e., without bend 22, under force. When the force is removed, guidewire 16 returns to the relaxed, bent configuration.

Guidewire 16 can be constructed of spring steel that can be deformed into a relatively straight configuration when withdrawn into catheter 12, but which springs back to its bent configuration when extruded from catheter 12 and released from constraint. Another way is to construct guidewire 16 of superelastic nitinol and take advantage of the martensitic transformation properties of nitinol. Guidewire 16 can be inserted into catheter 12 in its straight form and kept cool within the catheter by the injection of cold saline through catheter 12 and over guidewire 16. Upon release of guidewire 16 into the bloodstream, it will warm up and change to its austenite memory shape based on the well-known martensitic transformation by application of heat and putting the material through its transformation temperature.

Guidewire 16 can also be made out of a composite such as a nitinol tube within the guidewire structure. In this fashion, the martensitic or superelastic properties of nitinol can be combined with the spring steel characteristics of the spring and lead to a desirable composition. Other suitable materials for guidewire 16 include copper, constantin, chromel or alumel.

Figure 2:
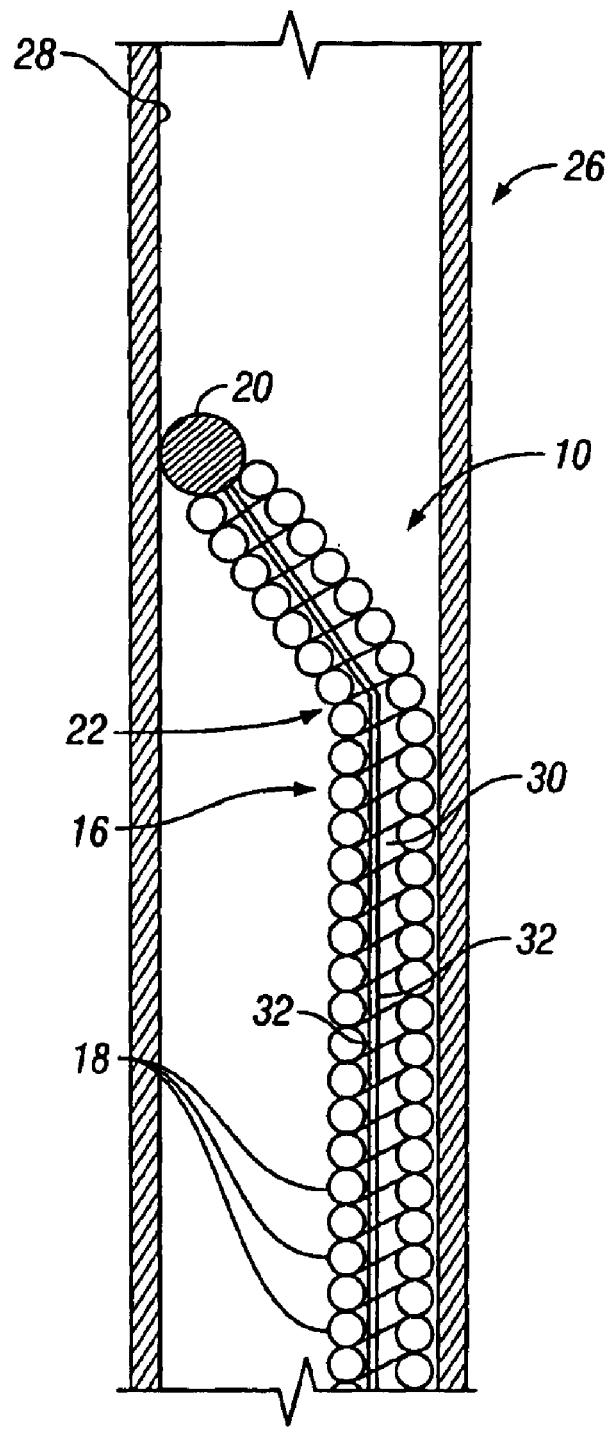
FIG. 2 is a longitudinal sectional view of an arterial hollow body organ in which the embodiment of FIG. 1, also shown in longitudinal section, is deployed.

FIG. 2 shows device 10 deployed in a hollow body organ comprising an arterial blood vessel 26 having an endothelium 28 forming the inner wall thereof. Only the distal portion of guidewire 16 that extends beyond catheter 12 is shown. Electrical conductors 32 extend through lumen 30 of guidewire 16. Conductor 32 is electrically insulated from the coils 18 of guidewire 16 so that guidewire 16 comprises one conductor and conductor 32 comprises another conductor or lead of the thermal sensor 20 which can be a thermocouple or thermistor. The conductors convey signals from the thermal sensor 20 to the proximal end of guidewire 16 for connection to appropriate signal processing apparatus that converts the received signals to a temperature indication.

Figure 3A:
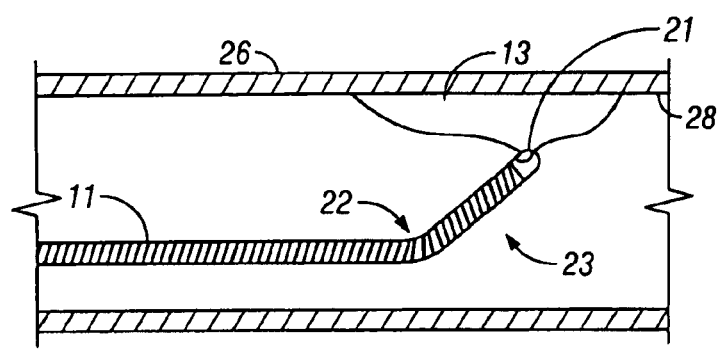
FIG. 3A is a longitudinal sectional view of a guidewire probe variation in which the sensor is positioned off-center or off-axis.

Although thermal sensor 20 is shown as extending along the center of the distal end of guidewire 16, sensor 20 is preferably positioned off-center or off-axis from the longitudinal axis of the guidewire. As shown in FIG. 3A, as guidewire 11 traverses along wall 28 within vessel 26, a lesion or obstruction 13 may force distal portion 23 to bend radially inward towards the longitudinal axis along bend 22.

Figure 3B:
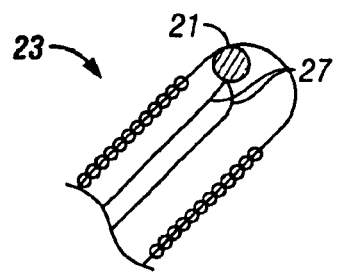
FIG. 3B is a cross-sectioned detail view of the probe of FIG. 3A.

Placement of thermal sensor 21 off-axis may allow for continuous contact and/or sensing between sensor 21 and wall 28 or lesion 13 despite having the center tip of distal portion 23 bent inwardly. FIG. 3B shows a cross-sectioned detail view of distal portion 23 where sensor 21, connected to conductors 27, is positioned off-axis near the distal tip.

In one use, the guidewire 16 and thermal sensor 20 of device 10, as shown in FIGS. 1 and 2, are inserted into the lumen 14 of catheter 12 from the proximal end, thereby constraining guidewire 16 in a substantially straight configuration with the thermal sensor 20 near the distal end of catheter 12. Using conventional percutaneous insertion techniques, access to the blood vessel 26 is obtained surgically. Catheter 12, with guidewire 16 and thermal sensor 20 disposed within, is advanced through the blood vessel 26 to the region of interest.

Catheter 12 is slowly withdrawn while guidewire 16 is secured against movement relative to the patient such that guidewire 16 emerges from the distal end of catheter 12 and reverts to the relaxed, bent configuration within the blood vessel 26. Alternatively, catheter 12 may be secured against movement relative to the patient and guidewire 16 may be advanced distally until it emerges from the distal end of catheter 12. Guidewire 16 remains substantially fixed in the axial direction relative to the blood vessel 26 as catheter 12 is withdrawn, with the re-formed bent distal portion of guidewire 16 springing gently radially outwardly into contact with the vessel wall 28.

In another use, catheter 12 may be omitted entirely from the deployment procedure. Rather, guidewire 16 may simply be inserted into the patient while in its relaxed configuration and advanced within the hollow body organ to the tissue region of interest. With catheter 12 omitted, the guidewire 16 may be advanced in its relaxed configuration, as mentioned, or it may be inserted within the patient in its substantially straightened configuration and be allowed to reconfigure itself by heating up while being advanced.

With guidewire 16 exposed and thermal sensor 20 lying in contact with the wall 28 of blood vessel 26, the thermal sensor 20 senses the localized temperature of the vessel wall 26 at the region where the thermal sensor 20 is situated. By slowly withdrawing guidewire 16, either into catheter 12 or simply withdrawing distally, while simultaneously rotating guidewire 16 about its longitudinal axis, thermal sensor 25 can be made to traverse a helical path around the inner wall 28 of the blood vessel 26, permitting temperature measurements to be taken at intervals of different regions of the vessel wall 28. Depending upon the response time of thermal sensor 20, which is preferably on the order of milliseconds, e.g., between 10 to 100 msec. and preferably less than 50 msec., rotation can be intermittent or continuous, as needed. By withdrawing and rotating the guidewire 16 at constant rates, e.g., at a scanning rate of about 50 mm/min with a linear or pull-back rate of between 0.3 to 10 mm/sec. and preferably 1 mm/sec. and at a rotational rate of between 1 to 100 rpm, and preferably between 10 to 100 rpm, and more preferably about 25 rpm, the location of the thermal sensor 20 relative to the distal end of the catheter 12 can be determined as a function of time, so that a temperature profile of the blood vessel 26 can be mapped, provided the response time of the thermal sensor is relatively short.

Figure 4A:
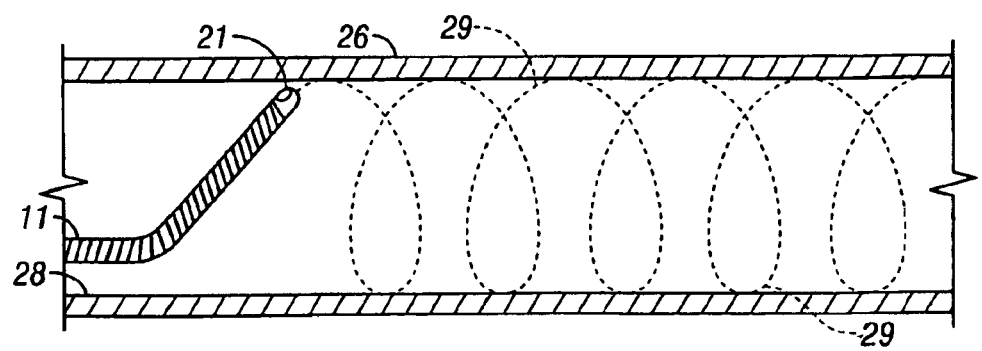
FIG. 4A is a longitudinal sectional view showing an example of a mapping or scanning path in which the rotational and withdrawal rates are constant.

One variation of a mapping procedure is shown in FIG. 4A where the rotational and withdrawal rates are maintained constant. The mapping or scanning path 29, i.e., the path traced by sensor 21 against vessel wall 28 as guidewire 11 is rotated and withdrawn, may be formed at a uniform rate.

To provide higher resolution measurements, the pitch of mapping or scanning path 29 may be tightened or shortened to provide for closer measurement readings, thereby producing a higher resolution profile. Yet to optimize the scanning profile and minimize the time involved in profiling a region of tissue, the device may be configured to automatically provide for lower resolution readings in non-critical areas and higher resolution readings in critical areas, e.g., where the temperature readings are elevated. One method of configuring the device may be to detect when a threshold temperature difference value between set variables, e.g., 0.05° to 0.5° C., is detected. When this threshold difference value is exceeded, this may be an indication of a lesion present within the tissue and the scanning path 29 of guidewire 11 may accordingly be tightened to produce the higher resolution profile.

Figure 4B:
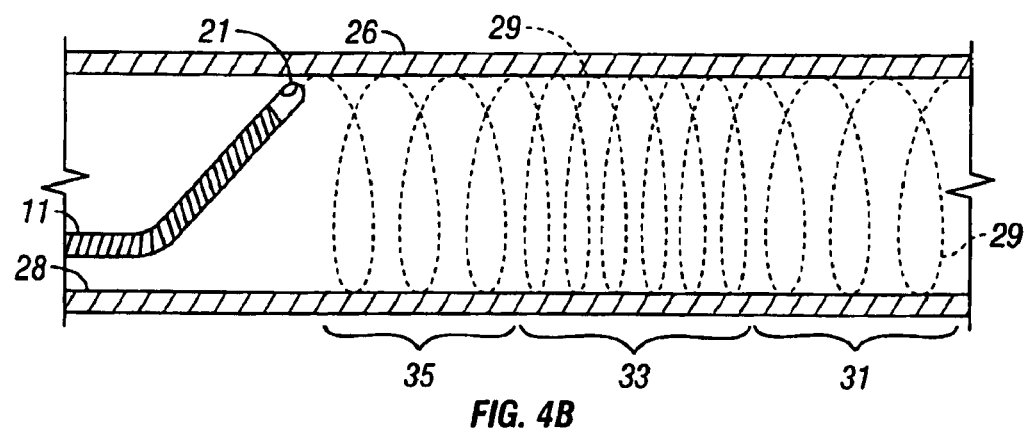
FIG. 4B is a longitudinal sectional view showing an example of a mapping or scanning path in which the rotational and/or withdrawal rates may be varied to provide for regions of higher and lower measurement resolution.

For example, during a mapping procedure as shown in FIG. 4B, the guidewire 11 may be rotated and withdrawn at an initial constant pitch. During this sensing period, scanning path 29 may provide for a relatively lower resolution temperature profile along region 31. When a temperature of the vessel wall 28 is measured by sensor 21 to exceed the predetermined threshold temperature difference, the pitch of scanning path 29 may be automatically reduced via a connected processor to produce the tightened scanning profile and thereby result in a higher resolution along region 33. As the scanning path 29 progresses, once the measured or sensed temperature difference value falls below the preselected threshold value, guidewire 11 may be configured to then automatically resume a lower resolution profile, as seen along region 35.

Once the mapping is completed, the guidewire 16 may be withdrawn fully into catheter 12, re-sheathed and constrained in a substantially straight configuration, if catheter 12 is utilized. Catheter 12 or guidewire 16 alone can then either be withdrawn from the blood vessel 26 or repositioned to another region of interest within the hollow body organ for further mapping of the temperature profile at that region.

Figure 5:
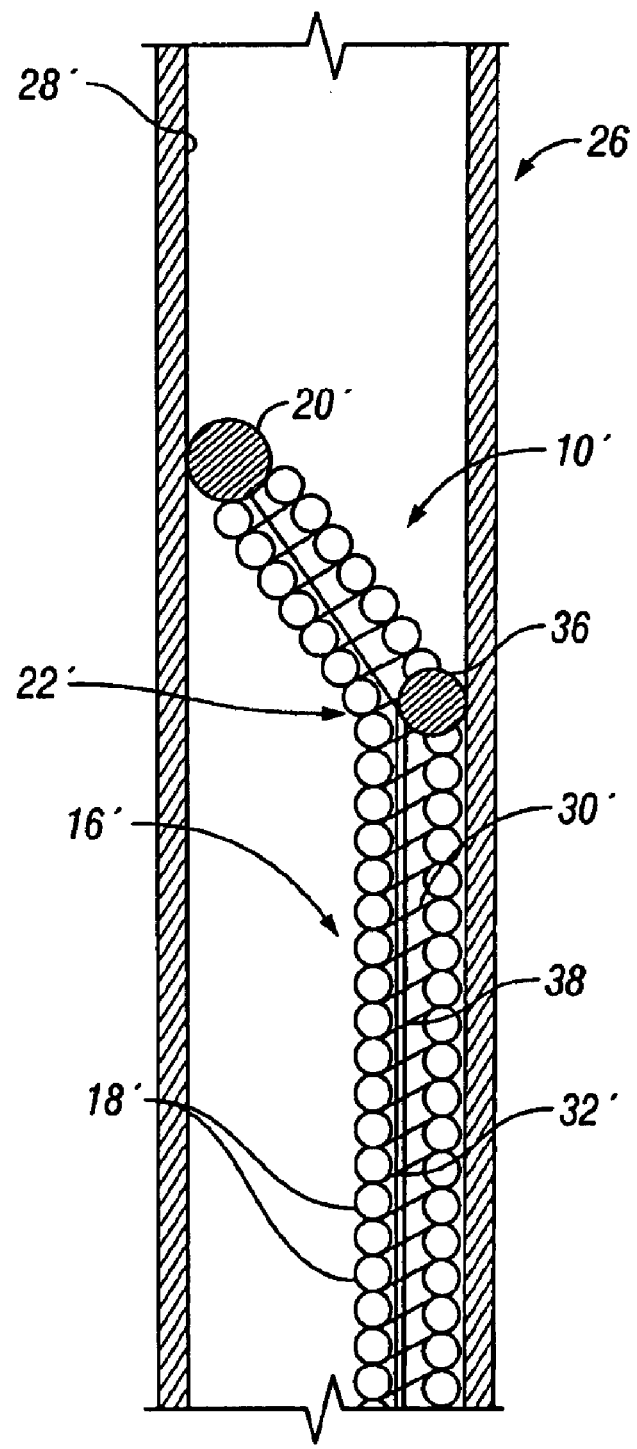
FIG. 5 is a longitudinal sectional view of an arterial hollow body organ in which another preferred embodiment of the present invention, also shown in longitudinal section, is deployed.

FIG. 5 shows a second preferred embodiment of a device 10' for profiling the wall of a hollow body organ. Device 10' can be deployed in a hollow body organ in a manner similar to the embodiment of device 10 shown in FIGS. 1 and 2 and described above with respect to structure and use. Components of device 10' that are similar in structure and function to corresponding components of device 10 of FIGS. 1 and 2 are designated by like primed numerals. The description of device 10 above applies also to device 10' unless described otherwise below.

Device 10' includes a second thermal sensor 36 disposed at the outside of bend 22' and exposed for contact with the inner wall 28' of vessel 26'. A second electrical conductor 38 is electrically insulated the conductor 32' and from the wire 18' of guidewire 16' so that guidewire 16' comprises one conductor and conductor 38 comprises another conductor of the thermocouple or thermistor of thermal sensor 36 for conveying signals from the thermal sensor 36 to the proximal end of guidewire 16 for connection to appropriate signal processing apparatus that converts the signals to a temperature indication. Wire 18' of guidewire 16' is a conductor common to thermal sensors 20' and 36.

Device 10' of FIG. 5 can be used in a manner substantially similar to the manner of use described above with respect to the devices above, except that thermistors 20' and 38 simultaneously traverse intertwined helical paths in contact with the inner wall 28' of hollow body organ 26'. Consequently, the temperature profile of the inner wall 28' can be mapped more quickly because data can be gathered from different locations simultaneously.

Figure 6:
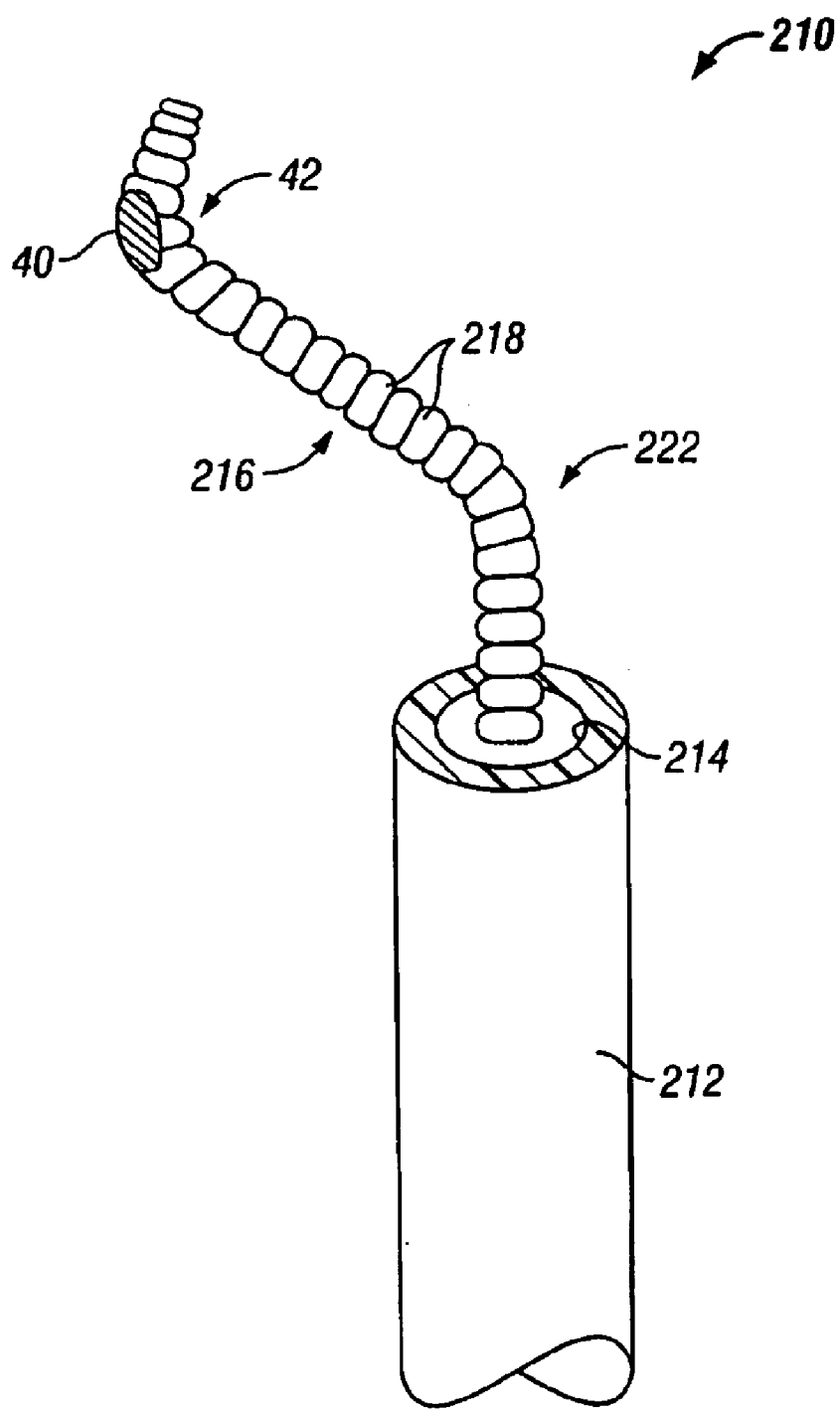
FIG. 6 is a perspective view of yet another preferred embodiment of the present invention.

FIG. 6 shows yet another preferred embodiment of a device 210 for profiling the wall temperature of a hollow body organ. Device 210 can be deployed in a hollow body organ in the manner described above with respect to the embodiments described above. Components of device 210 that are similar in structure and function to corresponding components of the devices above are designated by like reference numerals in the 200 series but having the same last two digits. The description of device 10 above applies also to device 210 unless described otherwise below.

Device 210 of FIG. 6 includes one thermal sensor 40 disposed at the outside of a dogleg bend 42 that is spaced distally from bend 222 and from the terminal end of guidewire 216. Thermal sensor 40 is exposed for contact with the inner wall 228 of vessel 226. An electrical conductor (not shown) is electrically insulated from the wire 218 of guidewire 216 so that guidewire 216 comprises one conductor and the electrical conductor comprises another conductor of the thermocouple or thermistor of thermal sensor 40 for conveying signals from the thermal sensor 40 to the proximal end of guidewire 216 for connection to appropriate signal processing apparatus that converts the signals to a temperature indication. Unlike the embodiments of the devices of FIGS. 1 to 5, device 210 includes only a thermistor at bend 42 and no thermistor at the terminal end of guidewire 216 or at bend 222.

Device 210 of FIG. 6 can be used in a manner substantially similar to the manner of use described above with respect to the devices of FIGS. 1 to 5.

Figure 7:
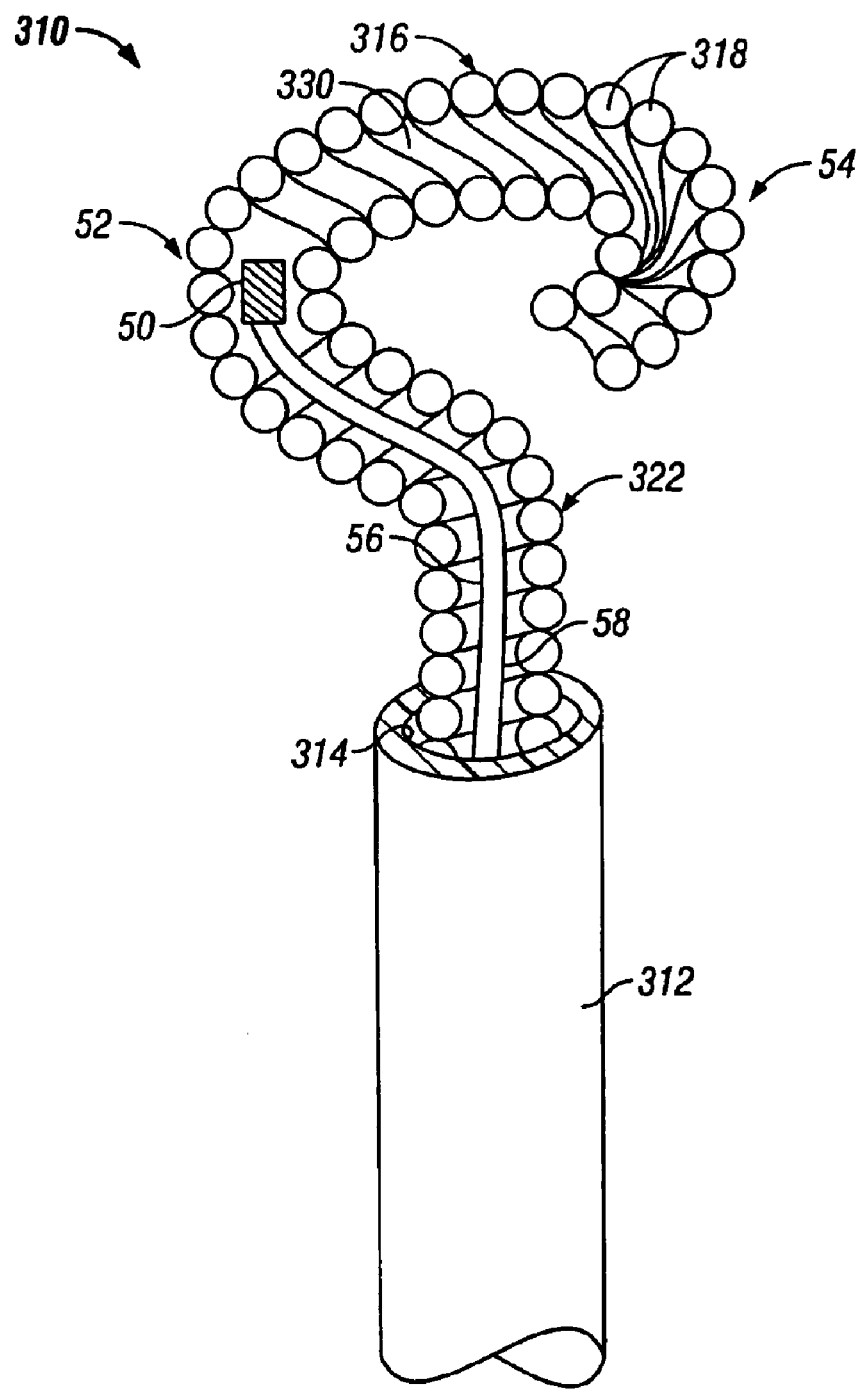
FIG. 7 is a perspective view, partially in section, of a further preferred embodiment of the present invention.

FIG. 7 shows a further preferred embodiment of a device 310 for profiling the wall temperature of a hollow body organ. Device 310 can be deployed in a hollow body organ in the manner described above with respect to the embodiments of the devices described above. Components of device 310 that are similar in structure and function to corresponding components of the above-described devices are designated by like reference numerals. The description of device 10 above applies also to device 310 unless described otherwise below.

Device 310 of FIG. 7, rather than having externally exposed thermal sensors as in the embodiments above, includes a thermal sensor 50 disposed within the lumen 330 of hollow guidewire 316 and in thermal contact with the coiled wire 318 that comprises guidewire 316. Thermal sensor 50 is located at bend 52 that is spaced between bend 322 and the distal end of guidewire 316. Guidewire 316 also includes bend 54 between bend 52 and the distal end of guidewire 316. Bends 322, 52 and 54 together cause the distal portion of guidewire 316 to assume the shape of a question mark when in a relaxed configuration. In such a configuration, bend 52 and bend 54 contact opposite sides of the inner wall of the hollow body organ. The spring nature of guidewire 316 urges bend 52 in contact with the hollow body organ. Insulated electrical conductors 56 and 58 are operatively connected to the thermocouple or thermistor of thermal sensor 50 for conveying signals from the thermal sensor 50 to the proximal end of guidewire 316 for connection to appropriate signal processing apparatus that converts the signals to a temperature indication.

Device 310 of FIG. 7 can be used in a manner substantially similar to the manner of use described above with respect to the devices.

Figure 8:
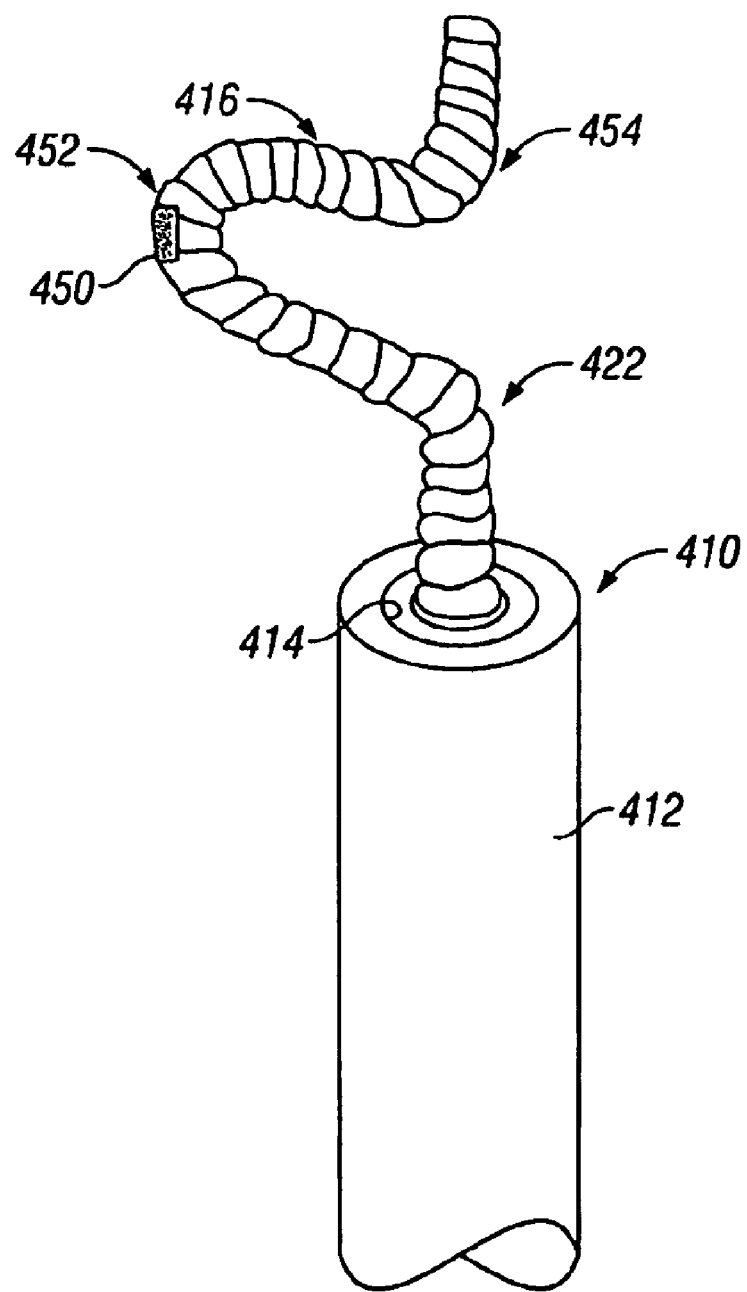
FIG. 8 is a perspective view of yet another preferred embodiment of the present invention.

FIG. 8 shows another embodiment of a device 410 for profiling the wall temperature of a hollow body organ.

Device 410 is an alternative configuration of the device 310 of FIG. 7, in which bend 454 extends in a direction opposite to that of bend 54, such that the terminal end portion of guidewire 416 extends axially away from catheter 412. Bend 454 serves a purpose similar to that of bend 54 of device 310 of FIG. 7, i.e., to assure that bend 452, at which thermal sensor 450 is located, remains in contact with the inner wall of the hollow body organ when deployed therein.

Figure 9:
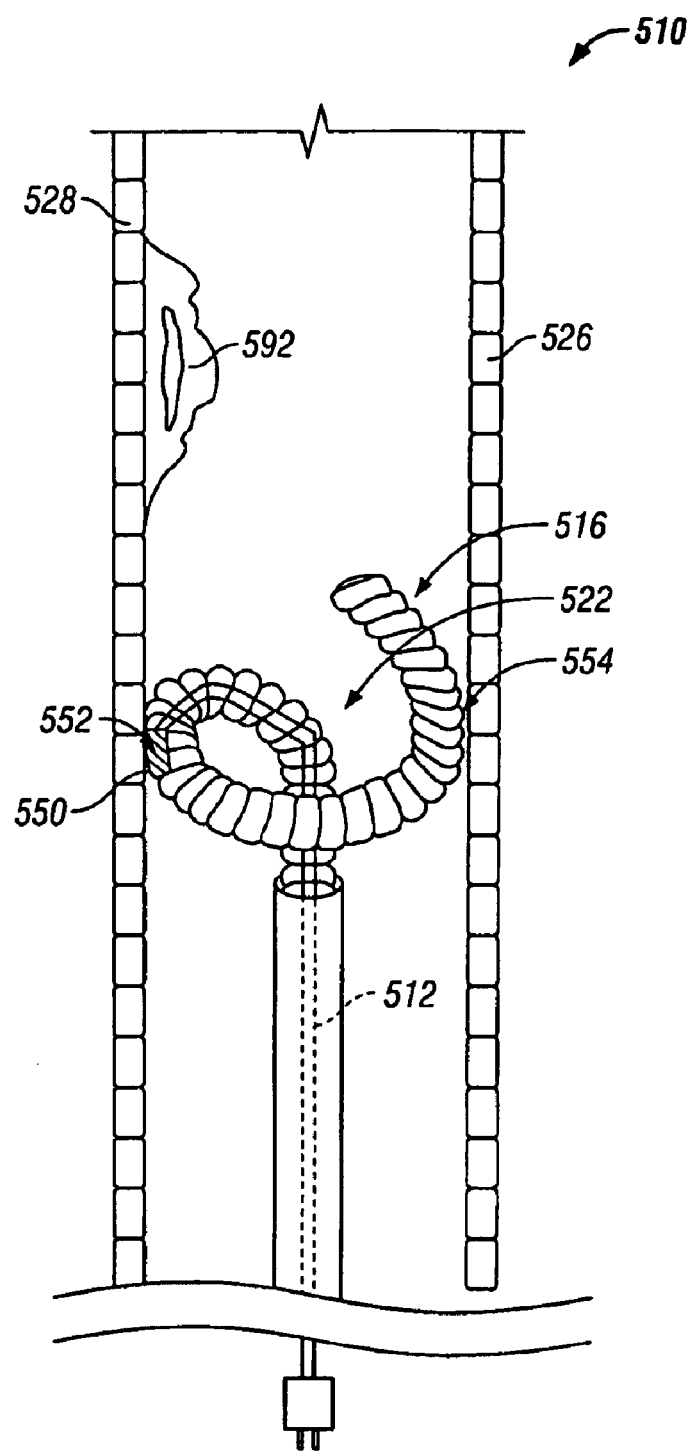
FIG. 9 is a longitudinal sectional view of an arterial hollow body organ in which another preferred embodiment of the present invention, shown in perspective, is deployed.

FIG. 9 shows yet another embodiment of the present invention. Temperature sensing device 510 is carried by hollow guidewire 516 which extends outwardly from the distal end of catheter 512 and includes thermal sensor 550, e.g., a thermistor at bend 552 spaced from bend 522 which is situated between the sensor-carrying bend 552 and the distal end portion of catheter 512. The distal end portion of guide wire 516 terminates in a generally crescent-shaped loop and is rotatable, continuously or continually, as desired, to sense the temperature of the endothelium 528 lining the wall of blood vessel 526 in the vicinity of plaque deposit 592.

Figure 10:
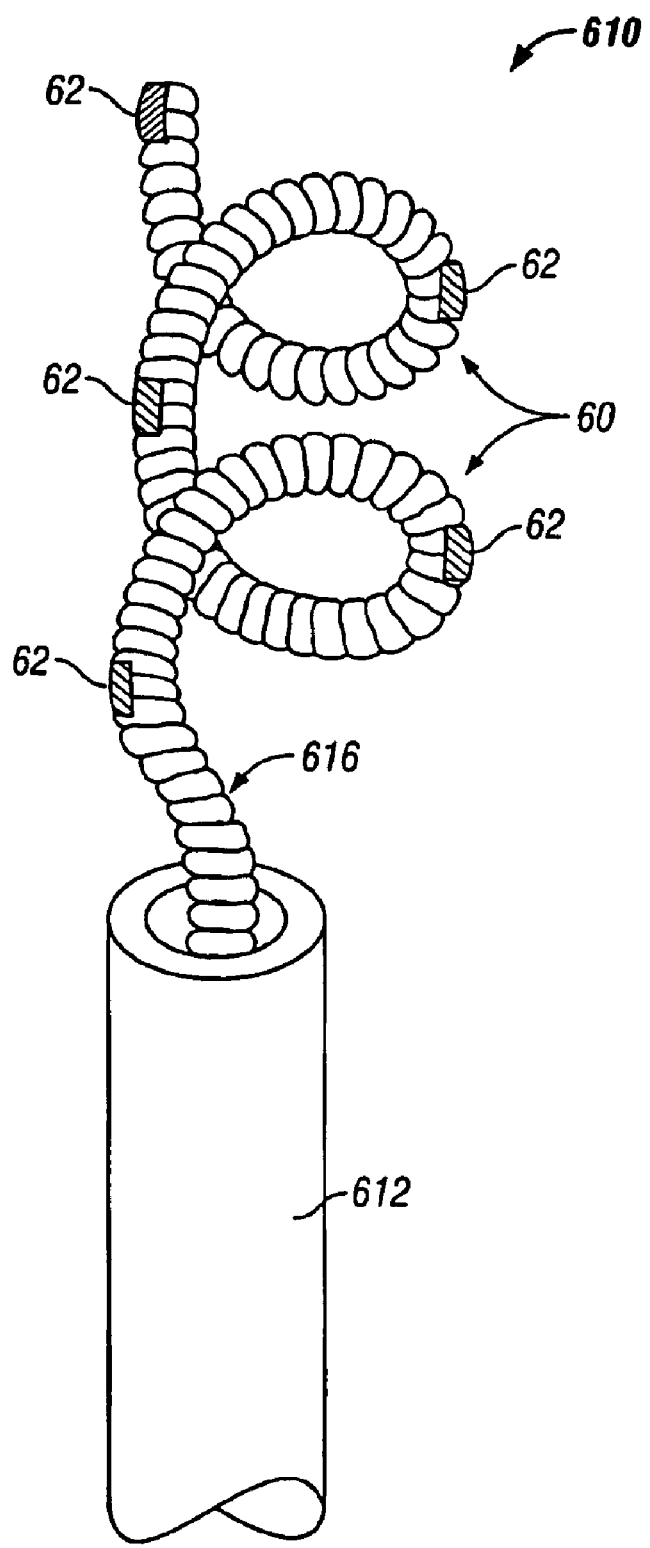
FIG. 10 is a perspective view of a further preferred embodiment of the present invention.

FIG. 10 shows a further embodiment of a device 610 for profiling the wall temperature of a hollow body organ. Device 610 comprises another alternative configuration of the device 310 of FIG. 7, in which guidewire 616 is shaped as a plurality of loops 60 with a plurality of thermal sensors 62 located within guidewire 616 at each location along the loops 60 that would contact the wall of the hollow body organ when disposed therein.

Figure 11:
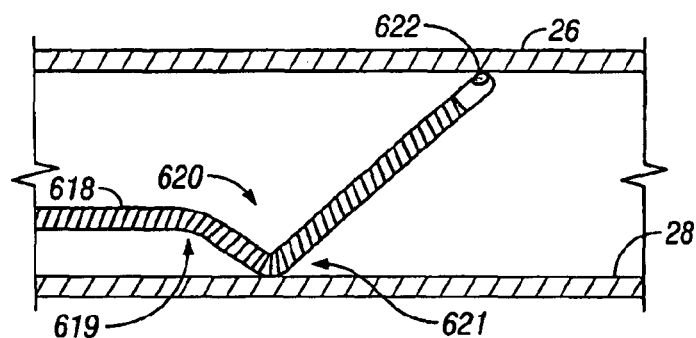
FIG. 11 is a longitudinal sectional view showing another variation of a guidewire having at least two bends.

FIG. 11 shows another embodiment of guidewire 618 which has two bends disposed within vessel 26. Guidewire 618 may be formed into a device which is configured to securely place the distal sensing tip against vessel wall 28. A contact region 621 is formed between guidewire 618 and vessel wall 28 by first bend 619. Guidewire 619 may then be configured with second bend 620 to extend sensor 622 against wall 28. With this variation, sensor 622 may be placed securely against wall 28 during rotation and withdrawal.

Figure 12:
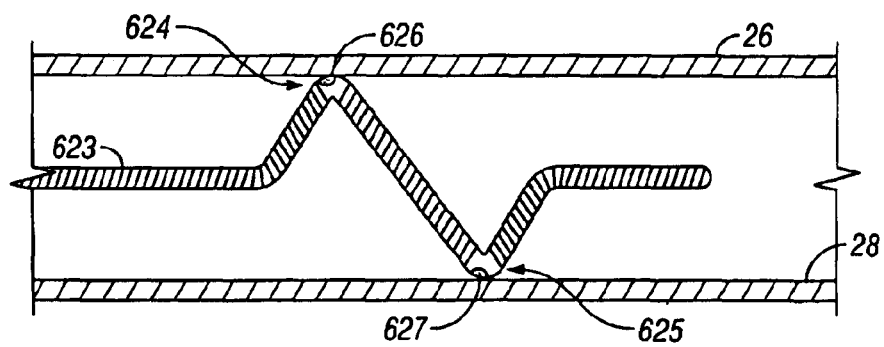
FIG. 12 is a longitudinal sectional view showing another variation of a guidewire having multiple bends and at least two sensors.

FIG. 12 shows a similar variation in guidewire 623 which may form first and second contact regions 624, 625 between first and second sensors 626, 627, respectively, against vessel wall 28. This variation may have at least two sensors 626, 627 formed to simultaneously detect opposite sides of wall 28 during a sensing procedure. This configuration may also allow for guidewire 623 to ensure contact between wall 28 and sensors 626, 627 since the two opposing contact regions 624, 625 may press in opposing directions against wall 28 with a gentle force.

Figure 13A:
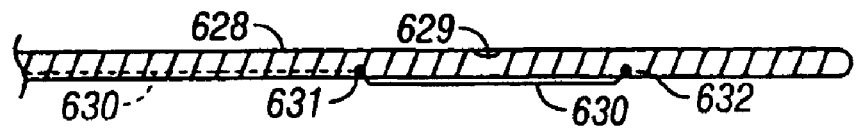
FIGS. 13A and 13B are longitudinal views showing alternative embodiments in which a guidewire probe may be reconfigured by active actuation into a shape having a bend portion.
Figure 13B:
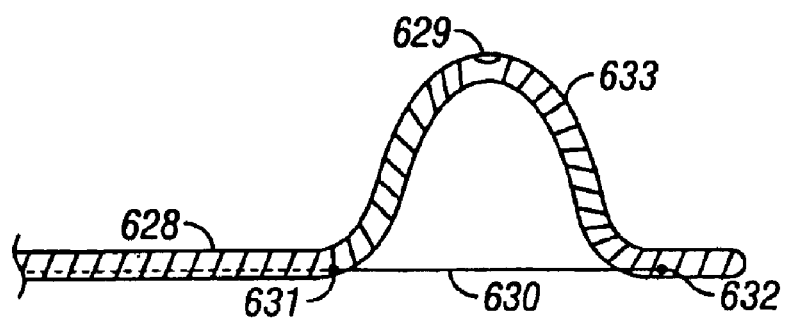

The following FIGS. 13A to 15B show alternative embodiments in which the guidewire probes may be configured to form their sensing configurations by active actuation alone or in addition to any reshaping which may occur by shape memory characteristics of the guidewires. As seen in FIGS. 13A and 13B, guidewire 628 may be formed in a straightened configuration with sensor 629 positioned at some location proximal of the distal tip. Pullwire 630 may be disposed within guidewire 628 along its length and exposed exteriorly of guidewire 628 between exit port 631 and anchor region 632. Sensor 629 is preferably positioned along guidewire 628 near the center portion between exit port 631 and anchor region 632. Guidewire 628 may be inserted into, e.g., the vasculature, in its straightened configuration and placed near the tissue region to be examined. Prior to examination, pullwire 630 may be pulled at its proximal end, preferably manipulated outside the body of the patient, such that a bend portion 633 is formed between exit port 631 and anchor region 632. As bend portion 633 is formed, sensor 629 is preferably extended radially relative to the longitudinal axis of guidewire 628 such that contact between sensor 629 and the vessel wall may occur. To help ensure that sensor 629 is extended on the outer curvature of bend portion 633, exit port 631 and anchor region 632 are preferably defined on guidewire 628 opposite to where sensor 629 is located.

Figure 14A:
FIGS. 14A and 14B are longitudinal views showing alternative embodiments in which a guidewire probe may be reconfigured by active actuation into a shape having a radially extended portion.
Figure 14B:
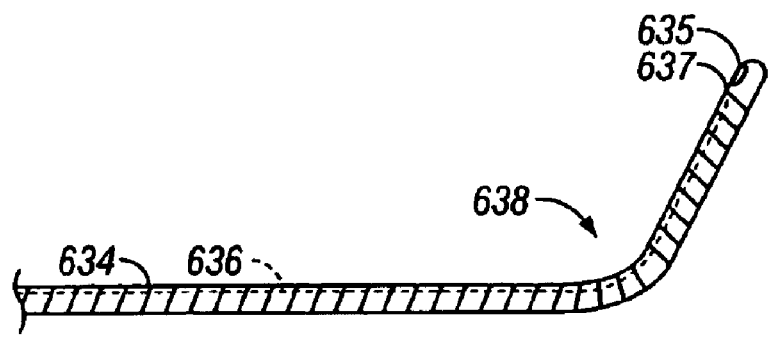

FIGS. 14A and 14B show another alternative embodiment in guidewire 634. Sensor 635 may be located near or at the distal end of guidewire 634 and pullwire 636 may be disposed within the length of guidewire 634 and anchored at anchor region 637 proximally of sensor 635. Prior to examination of the tissue region of interest, pullwire 636 may be manipulated to reconfigure the distal end of guidewire 634 to radially extend at bend region 638. At the end of the examination procedure, pullwire 636 may be relaxed and guidewire 634 may also be relaxed to reconfigure into its straightened shape.

Figure 15A:
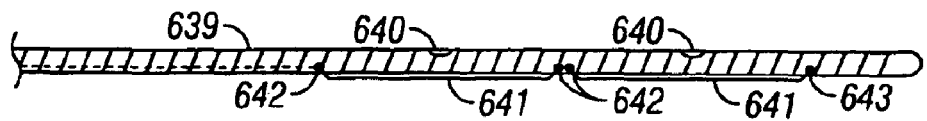
FIGS. 15A and 15B are longitudinal views showing alternative embodiments in which a guidewire probe may be reconfigured by active actuation into a shape having at least two bend portions.
Figure 15B:
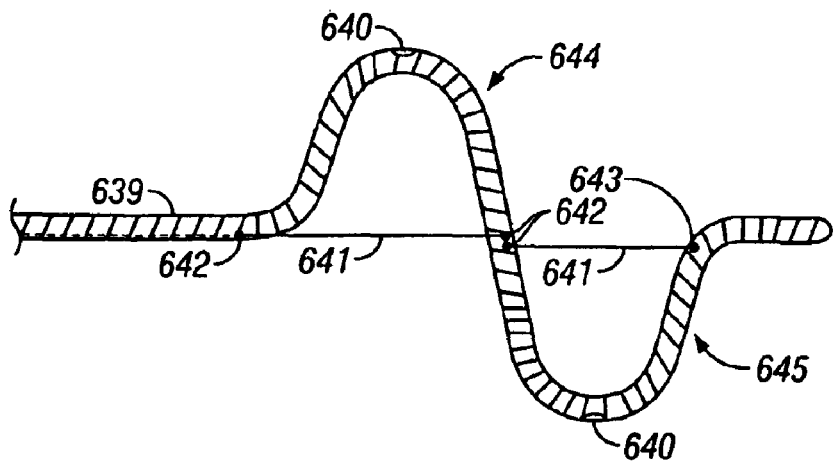

FIGS. 15A and 15B show an embodiment which is similar to that shown in FIG. 12 above. Guidewire 639 may be formed to have at least two sensors 640 spaced apart relative to one another along guidewire 639. Pullwire 641 may be disposed within the length of guidewire 639 and exposed exteriorly preferably between exit ports 642 and anchored to guidewire 639 at anchor region 643. As above, sensors 640 are preferably located near the central portions between the exit ports 642 and anchor region 643 and pullwire 641 is preferably located along guidewire 639 oppositely of sensors 640. Prior to examination, pullwire 641 may similarly be manipulated at its proximal end to reconfigure guidewire 639 into first and second bend regions 644, 645, respectively. Sensors 640 are preferably located along the outer curvatures of bend regions 644, 645 so guidewire 639 may undergo a torquing about its longitudinal axis to align sensors 640 accordingly as pullwire 641 is pulled.

Figure 16:
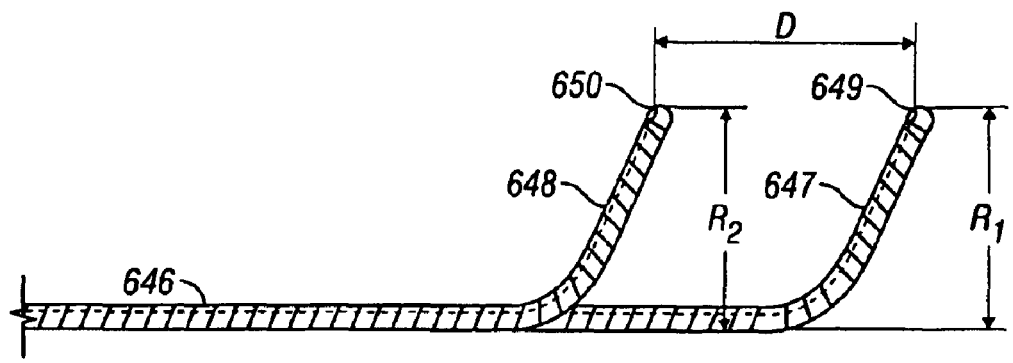
FIG. 16 is a longitudinal view showing another embodiment in which guidewire probe may have at least two radially extended probes linearly spaced apart from one another.

FIG. 16 shows another alternative embodiment in guidewire 646 which has linearly spaced probes separated by a distance D. As shown, first probe 647 has a distally located first sensor 649 at a first distance or radius $R_1$ relative to the guidewire 646 longitudinal axis and second probe 648 has a distally located second sensor 650 at a second distance $R_2$. Although this embodiment shows two probes, any number of linearly spaced probes may be used as practicable. Probes 647, 648 are preferably parallel with one another to ensure complete coverage during the scanning process, but they may alternatively be located at various angles relative to one another in the same plane or within different plane depending upon the desired configuration and application. The distance D between the probes 647, 648 may also be varied depending upon the desired coverage during scanning. Moreover, the radii may likewise be varied to suit the application. For instance, the radii shown has $R_1=R_2$; however, they may be varied such that $R_1<R_2$ or $R_1>R_2$ depending upon the scanning profile and the geometry of the tissue to be examined.

Figure 17:
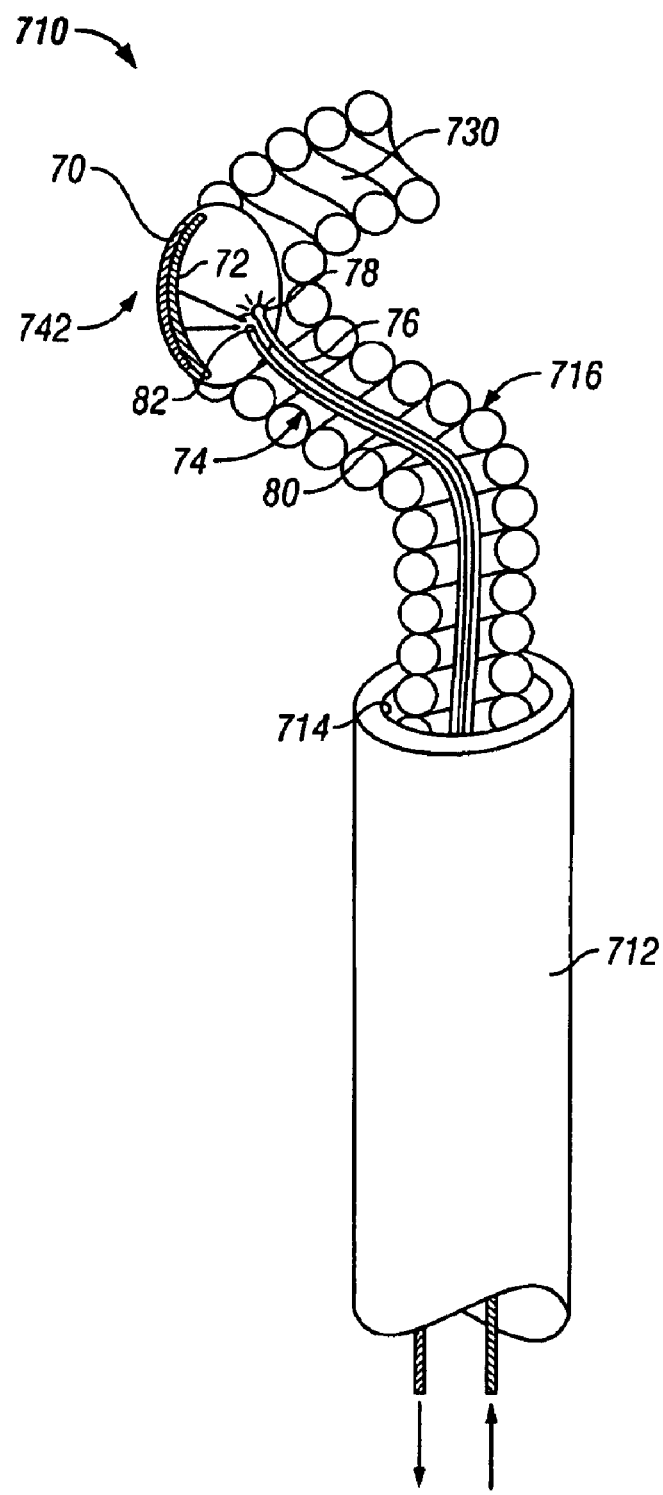
FIG. 17 is a perspective view of another preferred embodiment of the present invention.

FIG. 17 shows yet another embodiment of a device 710 for profiling the wall temperature of a hollow body organ. Device 710 includes a lumened catheter 712 and a hollow guidewire 716. The inner surface of lumen 730 of guidewire 716, at a bend 742 similar to bend 42 of device 210 of FIG. 6, is lined with a layer of black paint 70 which is in turn lined with a thermochromic material 72 that is sensitive to a change of temperature of the guidewire 716. The color of the thermochromic material 716 varies as a function of temperature.

Disposed within lumen 730 of guidewire 716, inwardly of thermochromic material 72, is an optical probe 74 including an illuminating optical fiber 76 having a radially emitting diffuser 78 at the distal end thereof, and a sensing optical fiber 80 having a conically beveled distal end 82 for collecting light. An illuminating electromagnetic radiation source connected to the proximal end of illuminating optical fiber 76 provides illuminating radiation that is guided by optical fiber 76 to the region of interest within the hollow body organ, and diffused radially by diffuser 78 to illuminate the interior of lumen 730, particularly thermochromic material 72. The illuminating radiation can be in the visible, infrared or ultraviolet portions of the spectrum. Radiation from diffuser 78 is differentially absorbed and reflected by thermochromic material 72, according to the color of material 72 which is indicative of the temperature of guidewire 716 in contact with the wall of the hollow body organ in the region of interest.

The light reflected from thermochromic material 72, having wavelengths indicative of the color thereof, is collected by distal end 82 and directed toward the proximal end of sensing optical fiber 80. An appropriate optical reflectance spectrometry device connected to the proximal end of sensing optical fiber 80 generates an electrical signal indicative of the color, and therefore temperature, of thermochromic material 72.

Figure 18:
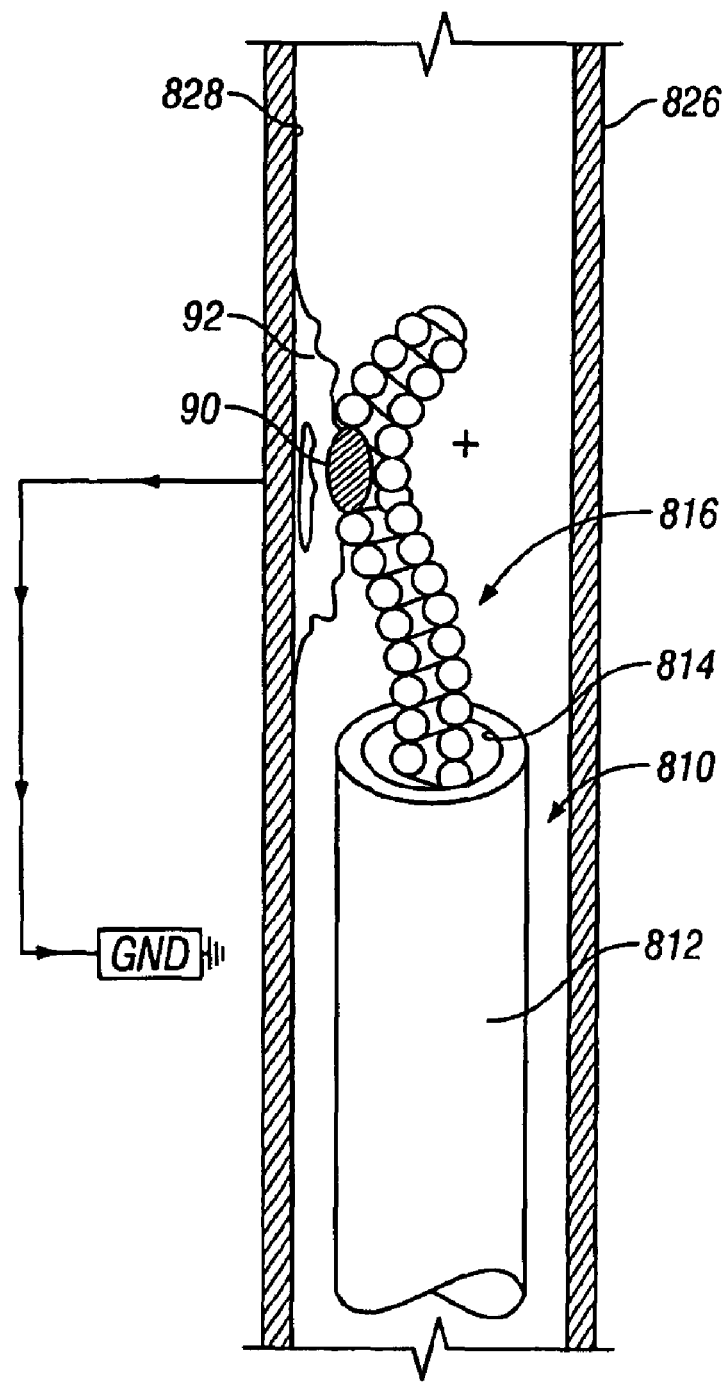
FIG. 18 is a longitudinal sectional view of an arterial hollow body organ in which yet another preferred embodiment of the present invention, shown in perspective, is deployed.

FIG. 18 shows yet another embodiment of a device 810 suitable for profiling the impedance of the wall of a hollow body organ. Device 810 includes a catheter 812 within which is disposed a guidewire 816 having a bend in the distal portion thereof. Device 810 is similar in configuration to the embodiment of device 210 of FIG. 6, and like components are indicated by like reference numerals in the 800 series but having the same last two digits. Unlike device 210 of FIG. 6, device 810 does not employ thermal sensing, but rather employs impedance sensing for profiling the wall of a hollow body organ. An electrode 90 at the outside of the bend of guidewire 816 is in electrical contact with guidewire 816 and in electrical contact with the inner wall 828 of the hollow body organ 826. Guidewire 816 comprises a conductor operatively connected to an external impedance measuring device that has a ground terminal electrically connected to the body in which the hollow body organ is located. A small electrical current is applied via guidewire 816 and electrode 90 to the inner wall 828 at the region of contact therebetween. The impedance of the electrical path through the body, including through the region of interest in the hollow body organ 826, can be measured and recorded. By moving guidewire 816 relative to the hollow body organ 826 as described above with respect to other embodiments, the impedance of the wall of the vessel 826 can be mapped. Any change of impedance along the wall 828 indicates the presence of an anomaly in the wall, such as a plaque 92.

Figure 19:
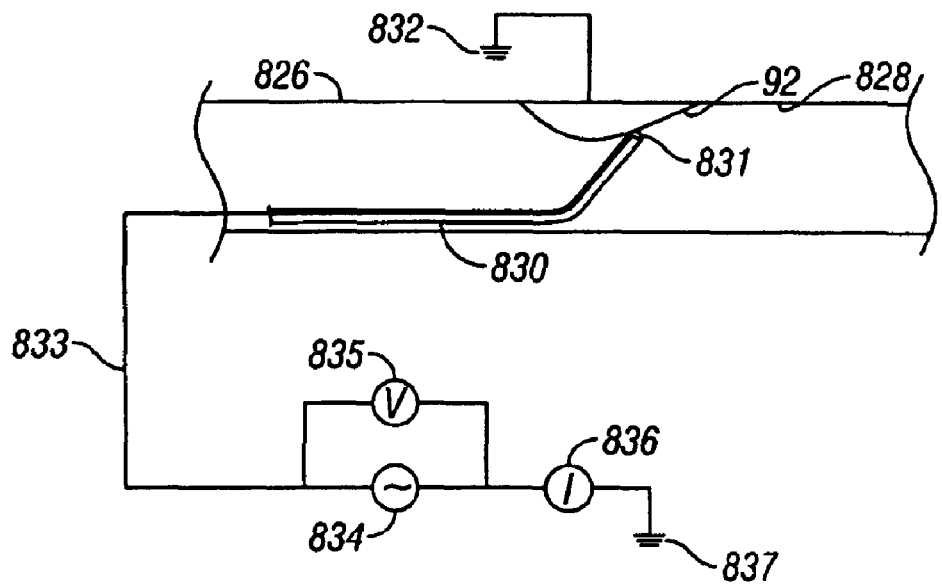
FIG. 19 is a longitudinal sectional view showing a variation in which impedance measurements may be taken to determine whether sufficient contact exists between the guidewire and the vessel wall.
Figure 20:
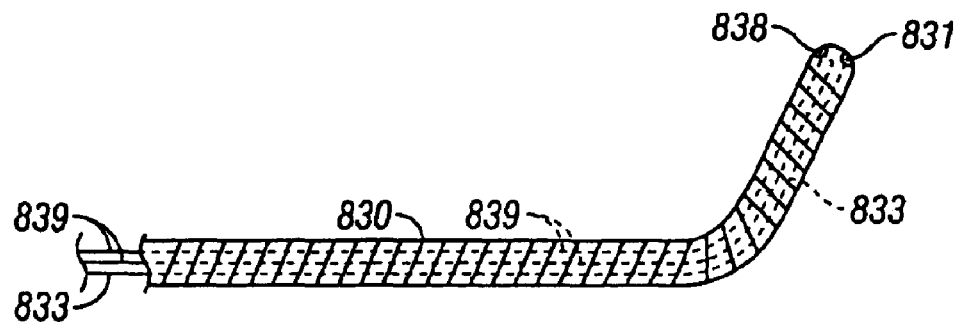
FIG. 20 is a detailed view of the probe of FIG. 19 showing a variation on the dual-sensor location.

Aside from detecting anomalies in the wall of the vessel, impedance measurements may also be used to provide real-time feedback for contact between the guidewire probe and the vessel wall. For instance, when the impedance value rises above a preselected threshold, this may be an indication of lost contact against the vessel wall 828 since the surrounding fluids, e.g., blood, and/or tissue will likely have a higher impedance than the tissue being examined. One variation using impedance measurements for ensuring contact against the vessel wall is shown in FIGS. 19 and 20. Similarly to FIG. 18 above, contact between guidewire 830 and plaque 92 or inner wall 828 may be ensured by monitoring the measured impedance. In this variation, an impedance sensor 831 may be disposed within the distal tip of guidewire 830 in communication with power source 834 via connection 833. Connection 833 may be any conventional electrical conductor or optical fiber if optical sensors are utilized. Power source 834 may be any type of power supply preferably capable of generating AC power.

In operation, a first voltage may be applied through the body or vessel 826, which is typically connected to electrical ground 832 either directly through, e.g., grounding straps, or indirectly through natural contact via the body of the patient. This first voltage, $V_1$, may be measured at voltage measurement location 835 and the resulting first current, $I_1$, may be measured at current measurement location 836, which is preferably taken between power source 834 and electrical ground 837. A second voltage at a second current may be applied through the body or vessel 826 and the resulting voltage, $V_2$, and current, $I_2$, may be measured at voltage and current measurement locations 835, 836, respectively. The ratio between the differences of the respective voltages and currents can then be calculated to give an impedance value, i.e., impedance $Z=\Delta V/\Delta I=(V_1-V_2)/(I_1-I_2)$. If contact were maintained between impedance sensor 831 and plaque 92 or vessel wall 828, a consistent impedance value may be maintained and used as an indicator of contact between the two. Yet if contact were broken, then the impedance value will vary and this may be used as an indicator of lost contact between guidewire 830 and the tissue.

One detailed example of a dual-sensor probe is shown in FIG. 20 which may be used for impedance measurement. As shown, the distal end portion of guidewire 830 may have the thermal sensor 838 in the distal tip, as described above, in communication with a proximally located detector and processor via conductors 839. A second sensor, impedance sensor 831, may be disposed adjacent or near thermal sensor 838, and connected via connection 833 as shown. Impedance sensor 831 may detect contact via electrical impedance, as described above, but it may also detect via alternative methods, e.g., ultrasound, infrared, laser light, electrical conductivity, etc. If impedance sensor 831 were configured to detect electrical impedance or conductivity, connection 833 will be conductors, but if sensor 831 were configured to detect via optical methods, e.g., infrared or laser light, optical fibers may accordingly be used as connection 833 to detect and transmit the optical signals. The methods for impedance detection of FIGS. 19 and 20 may be used with any of the various guidewire embodiments described herein.

Figure 21A:
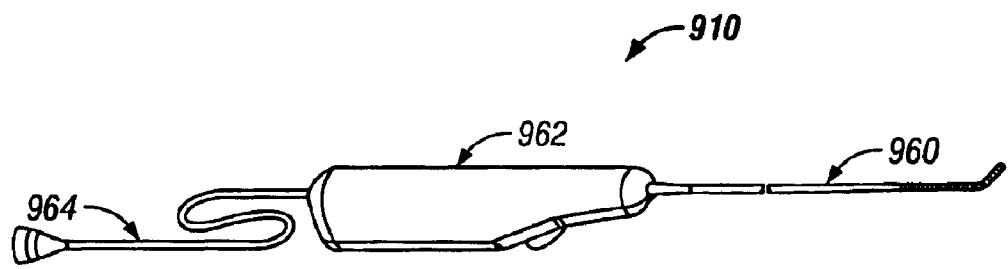
FIG. 21A is a perspective view of another device embodiment of the present invention.
Figure 21B:
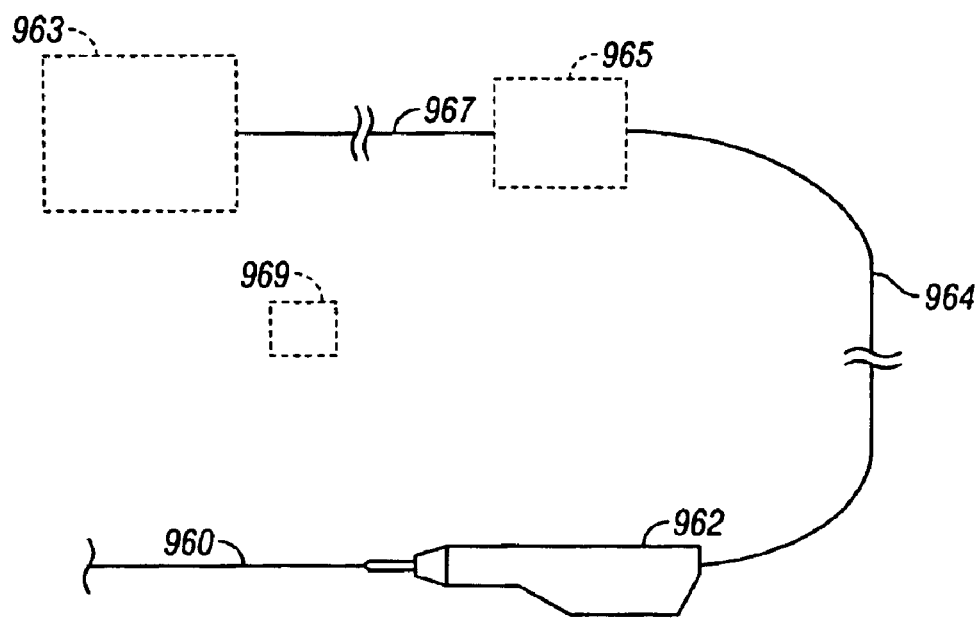
FIG. 21B is a schematic representation of a variation of a signal processor and controller connected to a probe actuator.

FIG. 21A shows a device embodiment 910 where a probe or guidewire 960 is adapted to be coupled to a detachable probe actuator 962 which, in turn, includes a cable 964 adapted to be coupled to a signal processing unit or the like. FIG. 21B shows schematically an example of an overall system for temperature sensing. As seen, probe actuator 962 may be connected via cable 964 directly to either the signal processor unit 963 or to the controller 965. The example shows the probe actuator 962 connected to controller 965, which may be used to control and/or record the advancement or withdrawal of the motors or actuators contained within probe actuator 962 (discussed below in further detail) used for manipulating the guidewire 960. Controller 965 may be connected via cable 967 to processor 963, e.g., a computer, which may be used to process and display signals received from guidewire 960 as well as to control the movement of guidewire 960 within the vasculature.

Prior to temperature acquisition, the probe system is preferably calibrated. The calibration may be performed through various methods. One example includes having two separate sensors for real-time calibration directly by a patient prior to use. One sensor may be placed in an orifice, e.g., the mouth, of the patient and an offset may be added to the measured value to estimate the core body temperature. The other sensor may be within the guidewire and used to acquire the temperature from the tissue region of interest.

Alternatively, the system may be calibrated in the factory and a programmed calibration factor may be provided to the physician or technician for final calibration prior to use by the patient. Another alternative may be to provide a calibration slug or pod 969 along with the system. Such a slug 969 may be made from a material, e.g., plastics or polymers, which may be consistently and uniformly heated or cooled to a predetermined temperature, e.g., 37° C., preferably within a protective case prior to calibration. Slug 969 is preferably configured to define a channel or station for receiving and holding the guidewire after the slug 969 has been heated to the desired temperature. The guidewire may then be calibrated prior to each use as the slug 969 may be preferably reused multiple times to generate a consistent calibration temperature.

Figure 22:
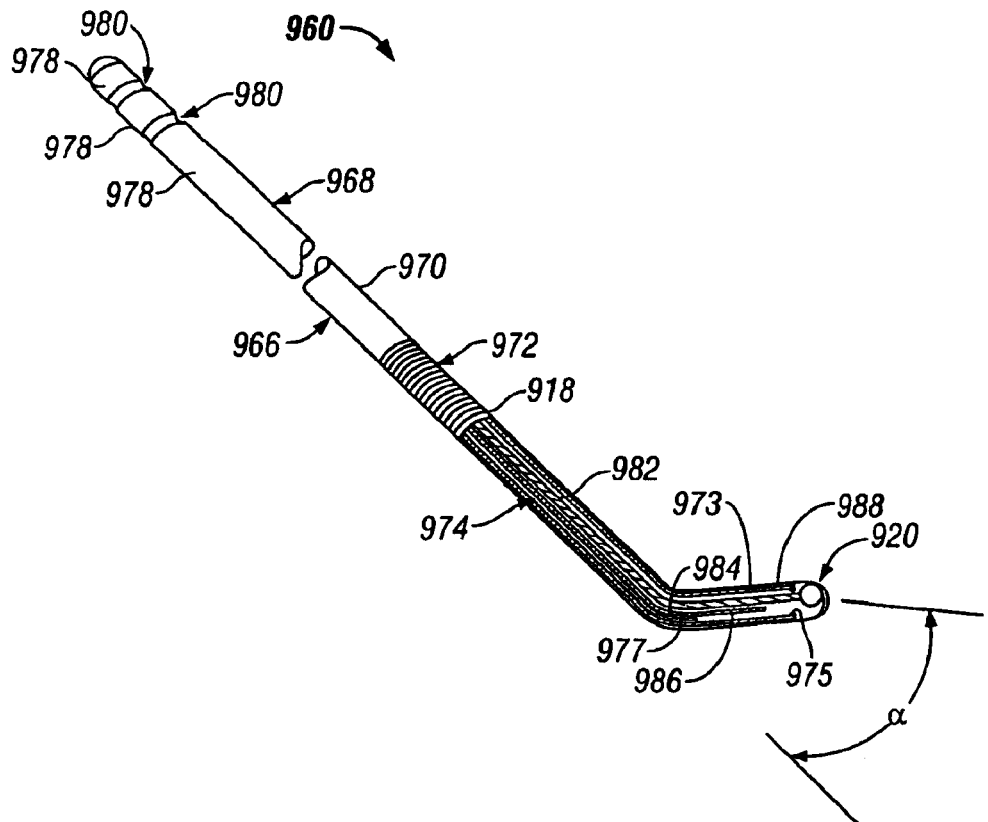
FIG. 22 is an exploded, broken perspective view of the probe of the device of FIG. 21A.

FIG. 22 shows the structure of the probe or guidewire 960 which includes a stem 966 having a proximal end portion in the form of a hollow, elongate flexible proximal hypotube 968, a mid portion in the form of a hollow, elongate, flexible mid hypotube 970 unitary with the tube 968, and a distal end portion unitary with the tube 970 and being in the form of a hollow coiled end tube 972 which has a bent tip portion or segment 973 and is composed of thin wire 918 which has been wound into small helical coils in a manner similar to that described with respect to the coiled guidewire 16 of the device 10 shown in FIG. 2. A transducer 920 is disposed within the interior of the terminal tip 973 of the distal coiled end tube 972. As described above with reference to the device 10 of FIG. 2, the transducer 920 can take the form of a thermal sensor such as a thermocouple, thermistor, or a radiation sensor. The transducer 920 can also, however, take the form of an instrument adapted to respond to inputs other than temperature or radiation such as, for example, displacement or force. A radiopaque marker band 975 in the tip 973 of the distal end tube 972 allows the exact location of the probe 960 to be tracked during use. Moreover, it is understood that the bent tip 973 of the distal end coiled tube 972 can be made of a material which is more radio-opaque than the material forming the remainder of the tube 972 to allow better visibility of the probe 960 as it is advanced through a blood vessel.

The distal coiled end tube 972 includes an elongate shaping mandrel 974 extending through the interior thereof generally between the distal end of the mid tube 970 and the transducer 920. The mandrel 974 comprises an elongate strip of metal or the like material having a distal tip portion 977 bent at an angle, α, generally between 10° to 90° relative to the longitudinal axis of the stem 966. In accordance with the preferred embodiment of the probe 960, the distal tip portion 977 of the mandrel 974 is bent at an angle, α, generally between 30° to 70° and more preferably between 40° to 60° relative to the longitudinal axis of the stem 966. The bent configuration of the mandrel 974 is, of course, imparted to the distal coiled end tube 972 of the stem 966. It has also been determined that the guidewire 16 disclosed in FIG. 2 should preferably also be bent at the same angles as described above with respect to the mandrel 974.

Although the mandrel 974 of FIG. 22 is permanently bent into its angled configuration, it is understood that the mandrel 974 can be constructed from the same types of shape memory materials described above with respect to the guidewire 16 of FIG. 2 including, for example, spring steel or superelastic nitinol, so as to allow the mandrel 974 to move between straight and bent configurations in response to, for example, a change in temperature or the withdrawal of the coiled end tube 972 from a catheter 12 as shown in FIG. 2.

Although not shown in FIG. 22, it is also understood that the mandrel 974 can alternatively take the shape of any of the coils described and shown herein. Additionally, it is understood that the present invention encompasses any one of several different mandrel embodiments depending upon the desired application of the device. For example, in applications where a soft and flexible tip portion 973 is desired, the length of the mandrel 974 can be shortened such that it terminates short of the tip portion 973. Moreover, in applications where the tip portion 973 must have a particular stiffness or in applications where it would be desirable to be able to bend or flex the tip portion 973 to help direct the probe into tight openings, the distal tip 977 of the mandrel 974 can be flattened and/or made of a material different than the remainder of the mandrel 974.

A plurality of spaced-apart parallel bands or rings of electrical connectors 978 surround the proximal tube 968 adjacent the proximal terminus thereof. The connectors 978 are separated from each other by a plurality of spaced-apart parallel bands or rings of insulative material 980. In accordance with one embodiment of the invention, the rings of connectors 978 and insulative material 980 respectively are flush with the outer surface of the tube 968 to assist in the alignment of the contacts 978 with cooperating contacts (not shown) in the actuator 962. Although not shown, it is also understood that the proximal tube 968 may incorporate a reduced diameter segment defining a groove in the proximal tube 968 and that the connector rings 978 can surround the reduced diameter segment to further assist in the alignment of the contacts with cooperating contacts in the actuator 962.

Also, an elongate conductive wire 982 extends through the stem 966 between and in contact with the connectors 978 at one end and the transducer 920 at the opposite end for conveying appropriate signals from the transducer 920 to the connectors 978 and thereafter through the actuator 962 and the cable 964 and into the appropriate signal processing apparatus (not shown). An elongate strip of insulative material 984 extending through the stem 966 insulates the conductive wire 982 from the coils 918 and the tubes 968 and 970. Moreover, an elongate strip of insulative material 986 insulates the mandrel 974 from the coils 918 and the tubes 968 and 970. Another elongate strip of insulative material 988 insulates the mandrel 984 from the conductive wire 982.

Figure 23:
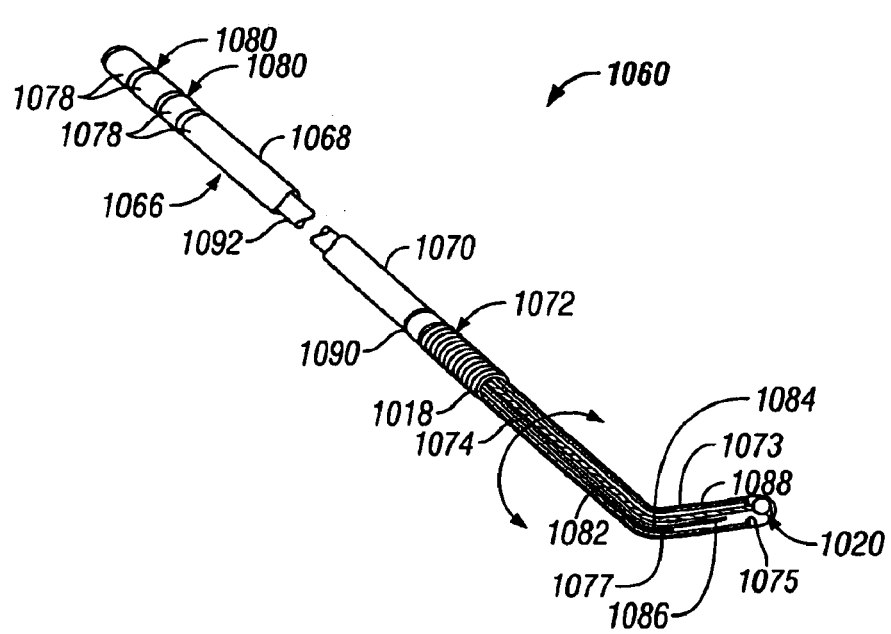
FIG. 23 is an exploded, broken perspective view of an alternate embodiment of the probe of the device of FIG. 21A.

FIG. 23 depicts another probe embodiment 1060 which is similar in structure to the probe 960 of FIG. 22. Components of probe or guidewire 1060 which are similar in structure and function to corresponding components of probe 960 are designated by like numerals in the 1000 series but have the same last two digits. The description of the probe 960 above applies equally to the probe 1060 unless described otherwise.

Specifically, the probe 1060 incorporates structure which allows the distal coiled tube 1072 to rotate relative to the mid-tube 1070. Particularly, the distal coiled tube 1072 is adapted to rotate about a rotary seal 1090 which separates the coiled tube 1072 from the mid-tube 1070, and the proximal and mid-tubes 1068 and 1072 respectively include an elongate actuation shaft 1092 extending therethrough and having a distal terminus (not shown) operably coupled for rotation to the proximal terminus (not shown) of the distal coiled tube 1072. Additionally, it is understood that the proximal terminus of proximal tube 1068 is adapted to be removably secured within the distal terminus of the actuator 962 shown in FIG. 21A and further that the actuator 962 incorporates motors therein (as described below) which is operably coupled to the proximal end of the shaft 1092 and adapted to impart a rotary and/or linear motion thereto which, in turn, is transferred to the distal coiled tube 1072. This, of course, allows the transducer 1020 in the bent tip portion 1073 of stem 1066 to traverse a circular path around the inner wall of the blood vessel in a manner similar to that described with respect to the earlier embodiment.

Figure 24:
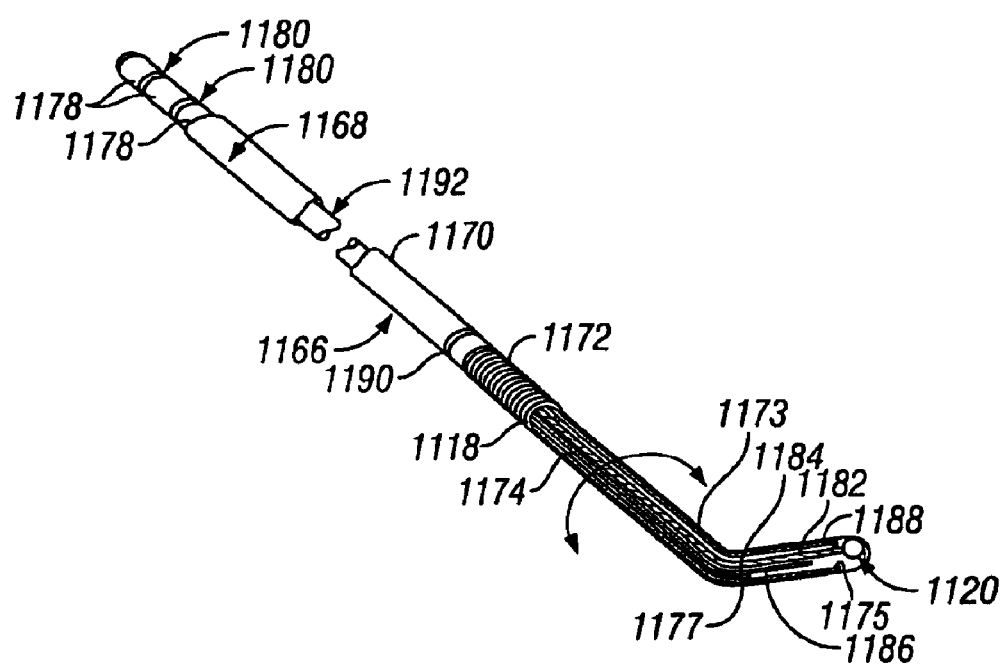
FIG. 24 is an exploded, broken perspective view of yet another alternate embodiment of the probe of the device of FIG. 21A.

FIG. 24 depicts a further probe embodiment 1160 which is similar in structure to the probes 960 and 1060. Component of probe 1160 which are similar in structure and function to corresponding components of probes 900 and 1060 are designated by like numerals in the 1100 series but having the same last two digits. The description of probes 960 and 1060 above applies equally unless described otherwise. Specifically, the stem 1166 is mounted for axial sliding back and forth movement about the actuator shaft 1192 extending therethrough. Moreover, in the probe 1160, the actuator shaft 1192 is hollow and, although not shown, it is understood that the elongate conductive wire 1182 extends through the distal coiled tube 1172 and then through the interior of the shaft 1192.

The probe 1160 also includes a plurality of spaced-apart, parallel bands or rings of electrical connectors 1178 surrounding the proximal end portion of the shaft 1192. The connectors 1178 are separated from each other by a plurality of spaced-apart parallel bands or rings of insulative material 1180. The connectors 1178 and bands of insulative material 1180 are flush with the outer surface of the rotating shaft 1192, and although not shown, it is understood that the proximal end of the conductive wire 1182 is connected to the connectors 1178.

It is understood that the probe 1160 and, more particularly, the proximal end portions of the shaft 1192 and the proximal tube 1168 are adapted to be removably fitted within the distal end of the actuator 962 (FIG. 21A) and further that the actuator 962 is adapted to incorporate, e.g., one or several motor-actuated screw drives, operably associated with the shaft 1192 and the stem 1166 to provide the combined rotational and axial probe movement which allows the transducer 1120 to traverse a helical path about the longitudinal stem axis in response to the activation of the actuator 962 to permit measurements to be taken at intervals of different regions of a vessel wall in the manner as described above with respect to the device 10 and FIG. 2.

Although not shown, it is also understood that each of the probe or guidewire embodiments described herein must be sufficiently flexible to be insertable within, for example, a blood vessel through a femoral artery access introducer and threaded into the coronary arteries and further that the various probe and guidewire embodiments must also have sufficient rigidity to ensure the rotation of the distal coiled tubes thereof in response to the rotation of the proximal end tubes thereof. In addition, the various probe and guidewire embodiments must provide support, i.e., directional control, for a catheter such as the catheter 12 shown in FIG. 2.

For example, because the balance between flexibility and rigidity is important to the effective operation of the various probe embodiments, it has been determined that the probe and guidewire embodiments herein should preferably be constructed such that the bent distal coiled end tubes thereof preferably incorporate a torque response of no more than about 0.4 ounce force inches (ozf in), and more preferably no more than 0.3 ozf in, in response to the torque which is applied to the proximal end tubes of the respective probe and guidewire embodiments. This particular distal coiled end tube torque response can be achieved by varying the profile and/or material and/or coating of any one of the tube sections or the mandrel.

Additionally, the stiffness or flexibility of the various guidewire or probe embodiments can be adjusted or varied also by changing the shape, profile and/or material of any one of the tube sections or mandrel. Depending upon the desired performance requirements, the tubes 968 and 970 of the device 910 may, for example, be made from either nitinol or stainless steel and the tube 972 can be shaped into either a flat ribbon or a flat wide ribbon to obtain the desired stiffness ratio.

For example, where a probe 910 with a soft and flexible coiled distal end tube 972 is desired, it has been determined that the tubes 968, 970 and 972 should be of a shape and/or material resulting in a relative stiffness ratio between the distal coiled tube 972, the mid-tube 970, and the proximal tube 968 of about 1:4,400:13,000, respectively. It has also been determined that in applications where a probe with a stiff distal coiled tube is desired, the tubes 968, 970 and 972 should have such a shape and/or be constructed of such material sufficient to provide a ratio of about 1:4:110 between the distal, mid and proximal tubes 968, 970, and 972, respectively. Moreover, testing has revealed that the preferred stiffness ratio between the respective distal, mid and proximal tubes forming the probe should be about 1:400:1200 to provide the desired distal end coiled tube torque response of no more than about 0.4 ounce force inches.

An example of the proximal end of a probe or guidewire, as shown in the various embodiments of FIGS. 22–24, is shown in FIG. 25A. The proximal end of the probe, which has been cross-sectioned for clarity, preferably comprises a connector assembly 2000 which comprises shaft 2002 having multiple contacts near the proximal end, e.g., proximal contact 2006 and distal contact 2008, which may be separated by indexing grooves 2004.

The sensor leads 2012 which extend down shaft 2002 to the sensor at the distal coiled tube, preferably terminate at each respective contact 2006, 2008. The proximal ends of the sensor leads 2012 may be electrically separated by any conventional insulative coating 2010 which may extend into indexing grooves 2004 to maintain the electrical separation. Indexing grooves 2004 may be formed such that they are non-coextensive with an outer surface of shaft 2002, i.e., grooves 2004 are formed such that they have diameters which are different, e.g., preferably less in diameter, than a diameter of shaft 2002. The probe may further extend proximally with a proximal extension 2014 to any desired length.

Figure 25B:
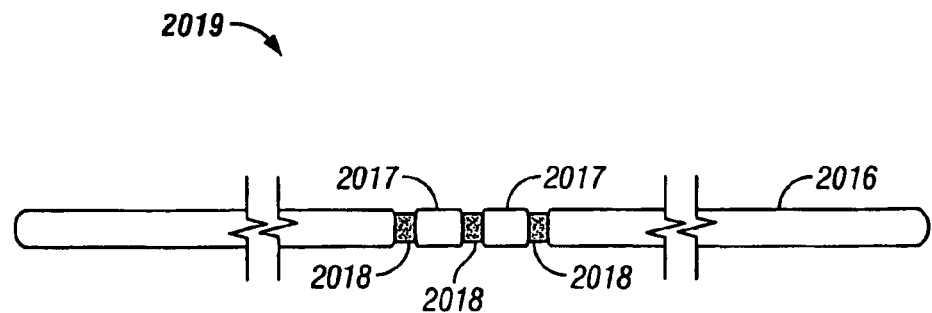
FIG. 25B is a side view of a variation on the probe in which the connector region is positioned near the mid-section of the wire.

Proximal extension 2014 may be extended a short distance as shown in FIGS. 22–24. However, another embodiment of the connector may include a probe having a length much longer than the lengths as shown in the figures above. As seen in FIG. 25B, probe 2016 may have a length with a mid-portion 2019 within which contacts 2017 and insulation 2018 may be situated. Contacts 2017 may be placed along the probe 2016 away from either the distal or proximal ends, and preferably near or at the mid-portion 2019 of probe 2016. Placement of the contacts 2017 within mid-portion 2019 may then allow for a probe 2016 having a length much longer, e.g., twice the normal length, than a length typically used. The additional length may then allow for the use of rapid-exchange type catheters to be guided over the body of probe 2016 for advancement through the vasculature.

Figure 26:
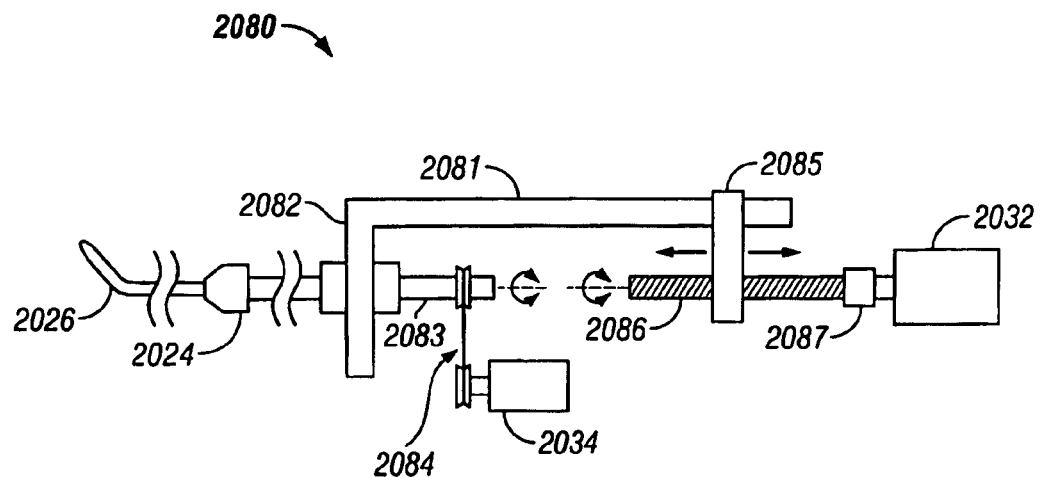
FIG. 26 is a schematic illustration of one variation of an actuator assembly which may be used to provide the rotational and axial movement for the probe.

Probe actuator 962, discussed above, may not only provide for rotational movement of the guidewire probe, but it may also provide for longitudinal movement. A schematic illustration of a variation of actuator 2080 is shown in FIG. 26. Rail guide or frame 2081 may provide an internal frame for supporting the various components within the handle of actuator 962. At a distal end of frame 2081, rotational shaft 2083 may be supported through interface 2082. Chuck 2024, to which probe 2026 may be connected, may be rotatingly connected to the distal end of rotational shaft 2083. The proximal end of rotational shaft 2083 may be connected to motor 2034, e.g., DC motor, which may provide the rotational torquing force to rotate chuck 2024 and probe 2026 about its longitudinal axis through, e.g., a pulley and cable assembly 2084, rotational gear assemblies, worm screw assemblies, etc.

At a proximal end of frame 2081, a second motor, e.g., stepper motor 2032, may be rotatingly connected via coupler 2087 to lead screw 2086, or any other device which can translate rotational motion into linear motion, e.g., worm screw assemblies, rack or internal gear and pinion assemblies, etc. Coupler 2087 may comprise any conventional coupling device which can transmit the rotational torque from a motor with minimal loss to another device such as lead screw 2086. A carriage assembly 2085 which is preferably connected to a proximal end of frame 2081 is preferably configured to receive lead screw 2086. Lead screw 2086 is preferably received through carriage 2085 within a threaded hole such that rotation of lead screw 2086 in a first rotational direction translates carriage 2085 and frame 2081 in a first linear direction and rotation of lead screw 2086 in a second opposite rotational direction translates carriage 2085 and frame 2081 in a second opposite linear direction. Thus, a controlled linear motion of probe 2026 may be provided by controlled rotation of motor 2032. Control of motors 2032, 2034 may be provided by a processor and/or controller as described above.

Although the actuators are shown as motors, e.g., DC or stepper motors, alternative actuators may include any type of practicable device which can be used to convert mechanical energy into rotational or longitudinal motion for the probes. For instance, screws or thumbscrews may be used to manually impart motion to the probe and guidewire apparatus. Alternatively, lead screw 2086, rotational shaft 2083, or chuck 2024, or any other component, may be manually manipulated to actuate movement of the probe without having to resort to the use of motors.

Figure 27:
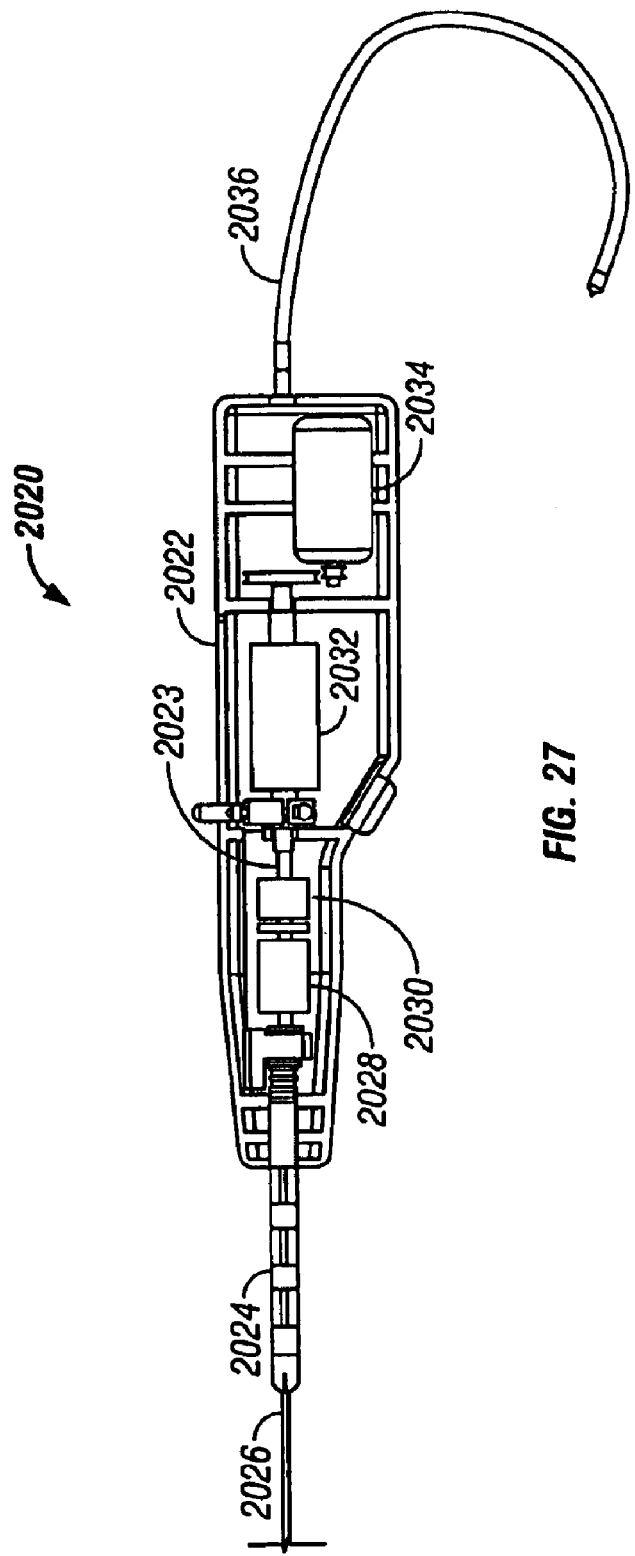
FIG. 27 is a side view of one embodiment of the probe actuator with the cover partially removed.
Figure 28:
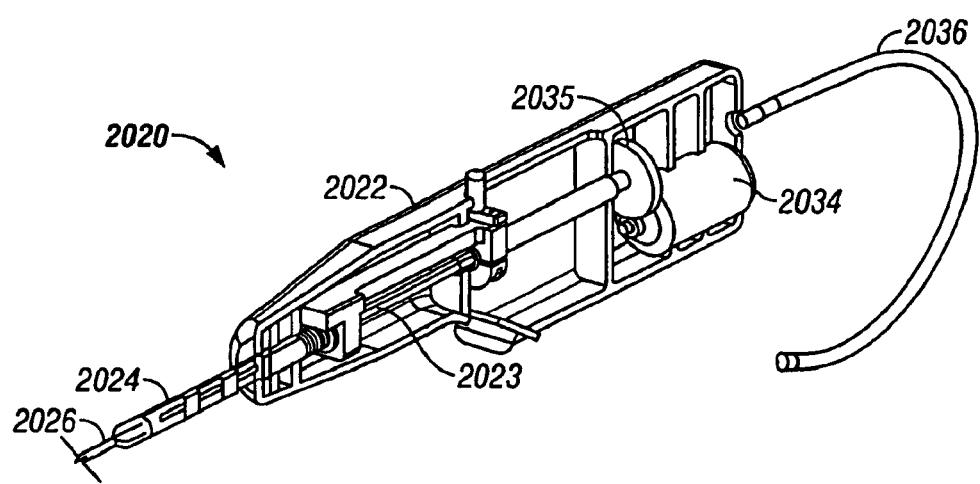
FIG. 28 is a perspective view of the probe actuator of FIG. 27 with some components removed for clarity.
Figure 29:
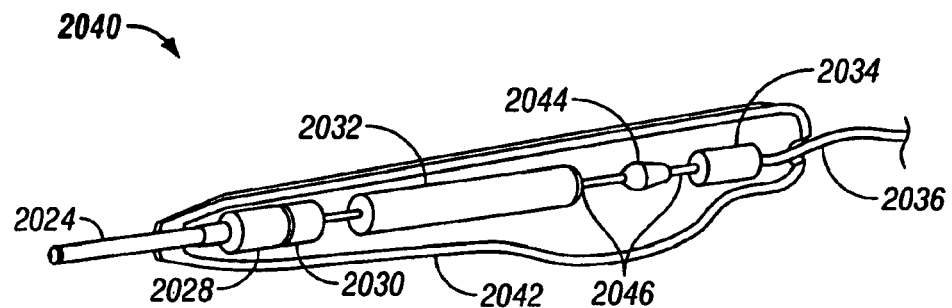
FIG. 29 is a perspective view of an alternate embodiment of the probe actuator with the cover partially removed.

FIGS. 27 to 29 show various embodiments which may incorporate actuator variation 2080, or various embodiments thereof, to effect motion. Various features may be omitted from the figures only for clarity. FIG. 27 shows a side view of one variation on probe actuator 2020 with the cover removed for clarity. Probe actuator 2020 comprises handle 2022 having an optionally detachable probe or guidewire chuck 2024. Guidewire chuck 2024, which is discussed in further detail below, is configured for mechanically and electrically receiving the proximal connection end of probe 2026 and chuck 2024 itself is in electrical communication with amplifier 2028. Probe 2026 is configured to rotate about its longitudinal axis, and accordingly, chuck 2024 is also configured to rotate about its longitudinal axis. Because chuck 2024 rotates, amplifier 2028 is also configured to rotate about the same axis as chuck 2024 while remaining in electrical contact to receive the signals from sensor leads 2012 during probe 2026 rotation.

As amplifier 2028 rotates, it is preferably electrically attached to a non-rotating platform 2030 having a plurality of concentric contacts for transmitting the signals to an externally located processor, e.g., processor 963 in FIG. 21B. An optional motor, e.g., stepper motor 2032, may be used to distally advance or proximally withdraw probe 2026 through a known longitudinal distance using, e.g., actuator variation 2080 above. The distance traveled may be controlled and/or recorded via processor 963 and controller 965 of FIG. 21B. Probe actuator 2020 may also contain within the handle 2022 a separate motor, e.g., DC motor 2034, used for the rotational control of probe 2026. The motor 2034 may rotate, e.g., in this variation the central shaft 2023, which may also connect the chuck 2024 with probe 2026. Each of the motors may have encoders (not shown) to determine both the rotational and axial position of the probe. Motor 2034 may also be controlled via the processor 963 and/or controller 965 through signal cable 2036.

FIG. 28 shows an isometric view of probe actuator 2020 of FIG. 27 with various components removed for clarity. Motor 2034 may be seen connected to the rotational shaft 2023 via a rotational gear 2035. Shaft 2023 may also be seen optionally extending from the motor 2034 to the probe or guidewire chuck 2024.

FIG. 29 shows an isometric view of an alternative probe actuator 2040 which has had the cover partially removed for clarity. As shown, handle 2042 may contain the components as described above, e.g., chuck 2024, amplifier 2028, stepper motor 2032, DC motor 2034, etc. The variation 2040 seen has the DC motor 2034 positioned in-line with the other components in a collinear arrangement. Thus, motor 2034 may be aligned and mechanically connected via coupler 2044 to transfer the rotational motion via shafts 2046 to chuck 2024. This arrangement allows for the compact packaging of the components within an ergonomically designed handle 2042.

The chuck 2024 which acts as the interface between the probe actuator and the probe itself is preferably removable as a separate unit from the probe actuator and may optionally be disposable. It may be provided as a package with the probe or guidewire for use with different probe actuators to maintain the sterility of the probe and the chuck between different patients. FIG. 30A shows a side view of a chuck 2024 which has been removed from the probe actuator. As seen by the dashed lines, a probe insertion lumen 2050 is defined within the chuck 2024 for receiving the proximal end of the probe 2026. Within the insertion lumen 2050, there may be one or several contacts 2052 which are complementary to the contacts 2006, 2008 located on probe 2026.

Chuck 2024 may also be configured such that probe 2026 is mechanically seated securely within the insertion lumen 2050. Ensuring a secure mechanical fit can ensure good signal transfer between probe 2026 and the amplifier 2028. Moreover, the processor 963 may be configured whereby if the probe 2026 is not securely seated, any temperature readings will default to a null value or alternatively to a predetermined value which is well beyond normal readings to indicate a faulty connection in the system.

Moreover, the insertion lumen 2050 may further define a stop or a barrier within for halting the insertion of the probe 2026 within the lumen 2050 at the desirable position such that the contacts are fittingly aligned with one another. When the contacts are desirably aligned, the electrical signals taken by the probe 2026 may be transferred through the chuck 2024 with minimal noise and interference. The proximal end of the chuck 2024 may define an attachment 2054 for connection to the probe actuator in which the attachment region 2054 defines several contact regions. These regions are configured to allow for the transfer of signals from contacts 2052 to an electrically connected amplifier while chuck 2024 rotates about its own longitudinal axis during signal acquisition.

Figure 30B:
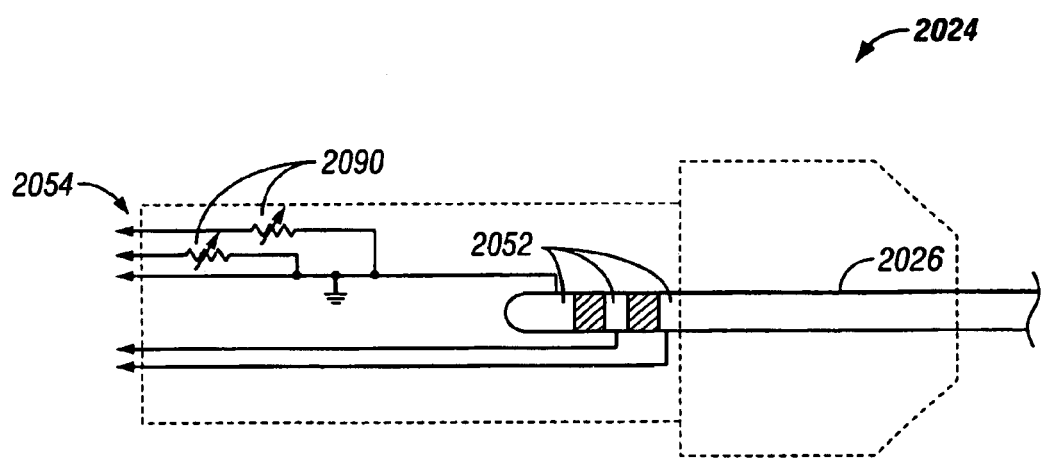
FIG. 30B is an electrical schematic showing one variation of the chuck from FIG. 30A which may be self-calibrated.
Figure 30A:
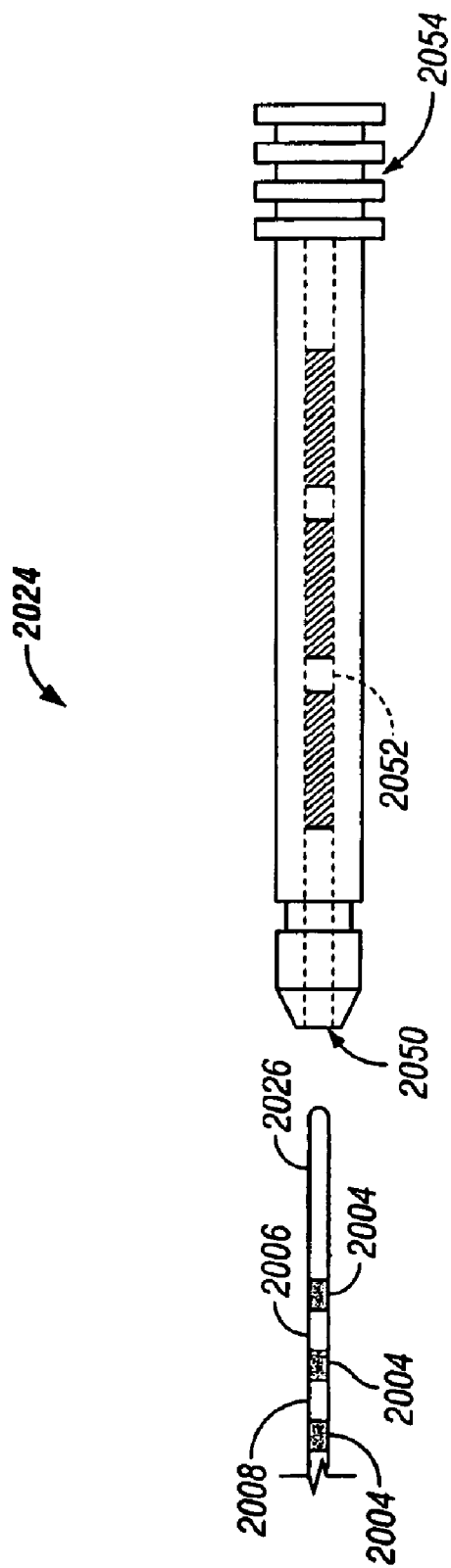
FIG. 30A is a side view of an embodiment of the probe chuck.

FIG. 30B shows one variation of an electrical schematic of chuck 2024 from FIG. 30A which may be self-calibrated. As seen, with probe 2026 seated within chuck 2024, electrical contact may be made between contacts 2052 and probe 2026. Chuck 2024 may be configured to have variable resistors 2090, which may also be discrete resistors, in electrical communication between probe 2026 and attachment region 2054. Variable resistors 2090 can be used to determine a calibration factor for a given probe which may be provided along with a chuck calibrated to the probe. For example, a resistor value of, e.g., 1 to 1000 $\Omega$, can be selected to have 1000 discrete values. An arbitrary resistor value of, e.g., 500 $\Omega$, may be selected as a neutral point and any probe having calibration errors above this neutral point may be used with a resistor having a value above 500 $\Omega$ and any probe having calibration errors below this neutral point may be used with a resistor having a value below 500 $\Omega$. Variable resistors 2090 in any chuck 2024 may simply be adjusted accordingly to account for the calibration errors.

Figure 31A:
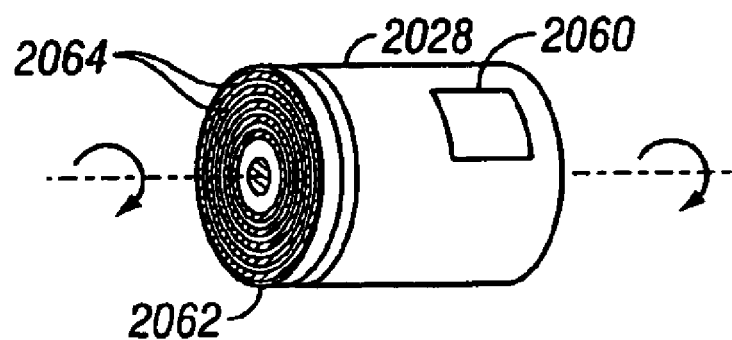
FIGS. 31A and 31B are perspective and end views, respectively, of an embodiment of a rotatable amplifier.
Figure 31B:
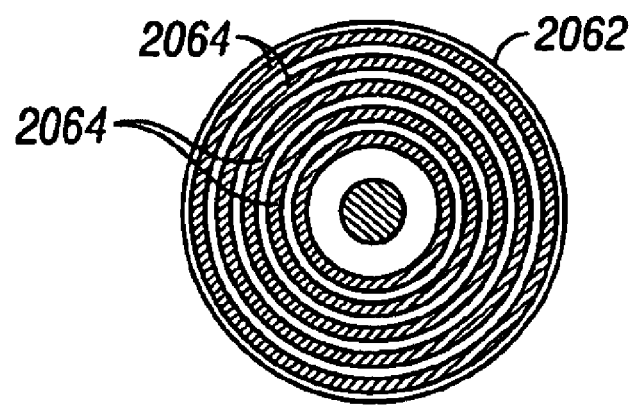

The amplifier 2028 of FIGS. 27 and 29 are shown in isometric and end views in FIGS. 31A and 31B, respectively. The amplifier 2028 is used to amplify the acquired signals taken from the tissue by the probe while rotating about a longitudinal axis as seen by the rotational arrows in FIG. 31A. As signals are electrically received by the amplifier circuitry 2060, they may be transferred via a rotating platform 2062 which is in electrical communication with amplifier 2028. The platform 2062, which is preferably circular in shape but may also be formed into other shapes, may have a plurality of contacts 2064 formed on one side of the platform 2062. The contacts 2064 may be formed into any number of concentric circles depending upon the number of contacts needed to transfer the signal. When the amplifier 2028 and the platform 2062 rotate during signal acquisition, the received signals may be transmitted through the contacts 2064 to brushes in corresponding contact without having to stop for signal transfer.

Figure 32:
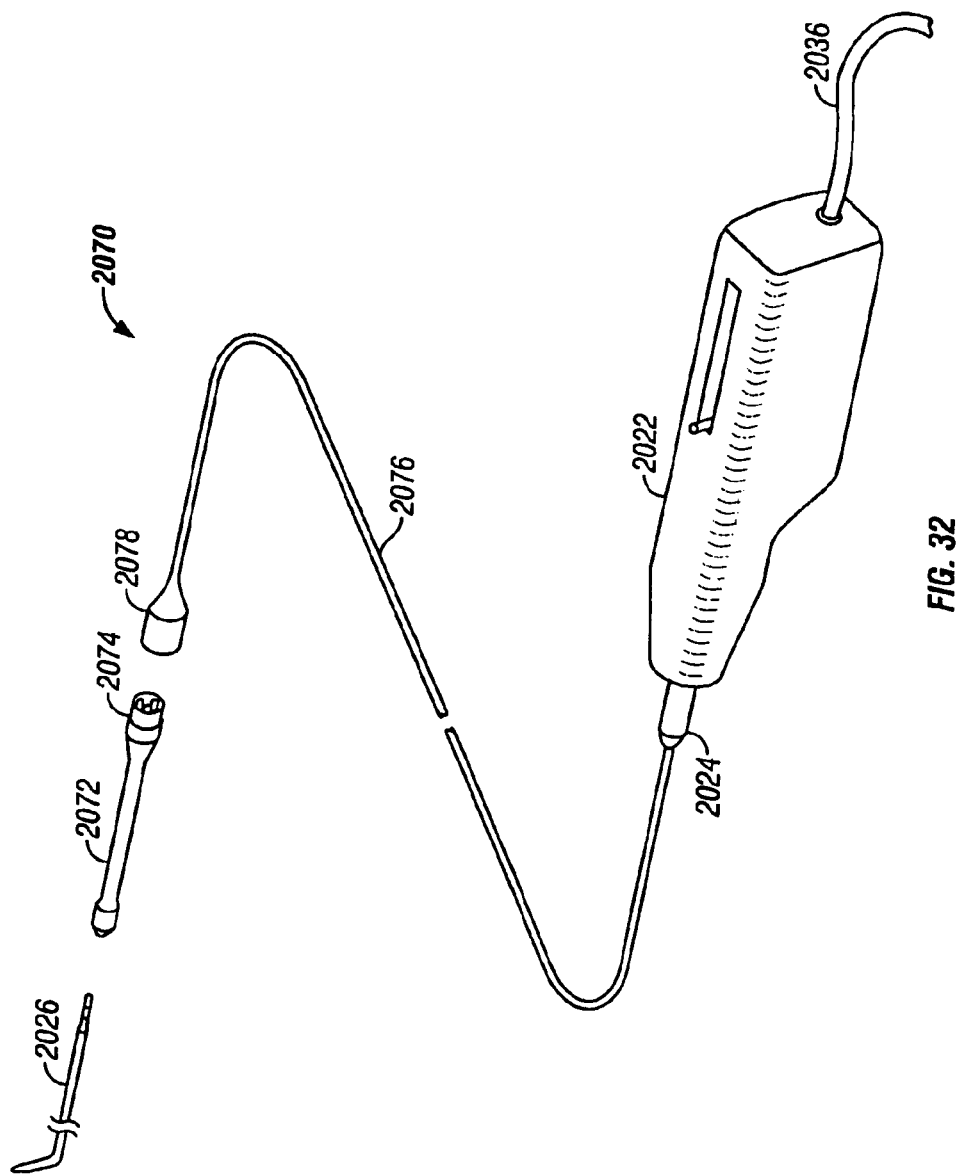
FIG. 32 is a perspective view of an alternate embodiment having a manually manipulatable assembly.

Signal processing and probe manipulation are preferably done by processor 963 and/or controller 965. However, manual operation of the probe may sometimes be desirable. To allow for easy manual manipulation, an intervening chuck assembly, an intervening connector cable, or a combination of both may be utilized. As seen in FIG. 32, an isometric view of a manually actuated probe assembly 2070 is illustrated with an optional intervening chuck 2072. The intervening chuck 2072 may be used to receive the probe 2026 in the same manner as described above and the chuck 2072 may have an optional connector 2074 for attachment to the intervening cable connector 2078. The intervening connector cable 2076 is preferably made of a polymeric material which is flexible enough to assume various curves but is stiff enough to transmit a torquing force along the length of the connector cable 2076. This can be accomplished through any variety of methods in constructing the connector cable 2076; for instance, metallic braids, reinforcing braids, or strands may be used in the construction of the cable. Alternatively, thermoset or thermoplastic polymers having a sufficient shear strength may be used alone or in combination with the various reinforcing methods.

The intervening chuck 2072 and connector cable 2076 may be used merely as an extension of the chuck 2024 in normal operation. When manual manipulation is desired, however, the physician or surgeon may manipulate the intervening chuck 2072 by hand to impart a rotational or longitudinal motion to the probe 2026 as necessary or desired. The intervening chuck assembly 2072 may be integrated directly with connector cable 2076. Alternatively, the chuck 2072 may be maintained as a separate device, as currently shown in FIG. 32, and attached separately to cable connector 2078 to maintain the sterility of the connector 2076 and handle 2022 prior to its use. Moreover, chuck 2072 may be omitted entirely and cable connector 2078 may be configured to receive and hold probe 2026 directly. Manual manipulation of probe 2026 may, in this case, be accomplished by rotating cable 2076, connector 2078 or probe 2026 directly.

Although the present invention has been described in detail in terms of preferred embodiments, no limitation on the scope of the invention is intended. The scope of the subject matter in which an exclusive right is claimed is defined in the appended claims.

What is claimed is:

1. A diagnostic probe suitable for insertion into a blood vessel comprising:
    an elongate stem including a proximal end portion and a distal end portion terminating in a coil and having at least a segment thereof biased away from the rotational axis of the probe and having a torque response of no more than about 0.4 ozf in.;
    a transducer mounted to the coil;
    a connector at the proximal end portion of the stem; and
    at least one conductor connecting the transducer to the connector.

2. The diagnostic probe of claim 1 wherein an elongate shaping mandrel extends through the coil.

3. The diagnostic probe of claim 1 wherein the coil is rotatable relative to the proximal end portion of the stem and the probe further comprises a rotatable actuation shaft extending through the proximal end portion of the stem and operably associated with the coil.

4. The diagnostic probe of claim 3 further comprising an actuator adapted for coupling to the proximal end portion of the stem and including a motor operably coupled to the actuation shaft.

5. The diagnostic probe of claim 3 wherein the proximal end portion of the stem defines a sheath slidable on the actuation shaft and operably coupled to the coil for allowing the axial reciprocal movement of the coil.

6. The diagnostic probe of claim 1 wherein the coil is biased at an angle between about 10° to 90° relative to the longitudinal axis of the stem.

7. The diagnostic probe of claim 6 wherein the coil is biased at an angle between about 40° to 60° relative to the longitudinal axis of the stem.

8. The diagnostic probe of claim 6 wherein the coil is biased away from the longitudinal axis of the stem.

9. The diagnostic probe of claim 6 wherein the coil is biased towards the longitudinal axis of the stem.

10. The diagnostic probe of claim 1 wherein the stem includes a mid portion between the proximal end portion and the coil and the flexural rigidity ratio between the proximal end portion and the mid portion and the coil is about 1 to 4,400 to 13,000, respectively.

11. The diagnostic probe of claim 1 further comprising a sensor mounted to the coil adjacent to the transducer for measuring an impedance against the blood vessel.

12. The diagnostic probe of claim 1 wherein the transducer is adapted to have a measurement response time between about 10 to 100 msec.

13. The diagnostic probe of claim 1 wherein the probe is adapted to be withdrawn longitudinally through the blood vessel at a rate of 0.3 to 10 mm/sec.

14. The diagnostic probe of claim 1 wherein the probe is adapted to rotate about a longitudinal axis defined by the elongate stem at a rate of between 1 to 100 rpm.

15. A device for sensing the profile of a hollow body organ, comprising:
    a hollow guidewire having a relaxed bent configuration defining an angle between about 10° to 90° relative to a longitudinal axis of the guidewire, and a contracted configuration; and
    a sensor connected to the guidewire and moveable therewith, the sensor being displaceable laterally relative to the longitudinal axis of the guidewire when the guidewire is in the relaxed configuration.

16. The device of claim 15 further comprising a catheter having a longitudinal axis wherein the hollow guidewire is slidingly disposable therewithin.

17. The device of claim 16 wherein the guidewire has the relaxed bent configuration when disposed externally of the catheter and the contracted configuration when disposed internally of the catheter.

18. The device of claim 15 wherein the guidewire is bent at an angle between about 40° to 60° relative to the longitudinal axis of the guidewire.

19. A diagnostic probe suitable for insertion into a blood vessel comprising a stem including a proximal end portion, a distal end portion and a mid portion therebetween, the ratio of the flexural rigidity of the distal end portion relative to the mid portion and the proximal end portion in the range of 1:(4 to 4,400):(110 to 13,000), respectively.

20. The diagnostic probe of claim 19 wherein the ratio of the flexural rigidity of the distal end portion relative to the mid portion and the proximal end portion is 1:4:110, respectively.

21. The diagnostic probe of claim 19 wherein the ratio of the flexural rigidity of the distal end portion relative to the mid portion and the proximal end portion is 1:400:1200, respectively.

22. The diagnostic probe of claim 19 wherein the ratio of the flexural rigidity of the distal end portion relative to the mid portion and the proximal end portion is 1:4,400:13,000, respectively.

23. The system of claim 1 wherein the transducer is a type selected from the group consisting of thermocouples, thermistors, radiation sensors, oxygen sensors, ultrasonic transducers, impedance sensors, pH sensors, and mechanical force sensors.

24. A system for determining the profile of a hollow body organ comprising:
    an elongate stem including a proximal end portion having a connector mounted thereto and a distal end portion having a detector mounted thereto, wherein at least a segment of the distal end portion is biased away from a rotational axis of the stem when in a relaxed configuration;
    a conductor extending through the stem between the detector and the connector;
    a processor in communication with the connector; and
    an amplifier in electrical communication with the proximal end portion of the stem, the amplifier being adapted to rotate about the rotational axis of the stem while amplifying signals received from the detector.

25. The system of claim 24 wherein the detector comprises a transducer.

26. The system of claim 24 wherein the connector comprises a plurality of spaced-apart bands of conductive material extending along the proximal end portion of the stem and separated therefrom by a plurality of bands of insulative material.

27. The system of claim 26 wherein the stem includes an outer surface and the respective bands of conductive and insulative material are flush with the outer surface of the stem.

28. The system of claim 24 further comprising at least one actuator attachable to the proximal end portion of the stem and adapted to provide rotational, axial, or both rotational and axial movement to the stem.

29. The system of claim 28 wherein the actuator comprises at least one motor coupled to the stem for providing a torquing force for rotating the stem about the rotational axis.

30. The system of claim 29 wherein the actuator is adapted to rotate about a longitudinal axis defined by the elongate stem at a rate of between 1 to 100 rpm.

31. The system of claim 29 wherein a rotatable shaft extends at least partially through the actuator between the motor and the proximal end portion which is operably coupled to the shaft for rotation therewith.

32. The system of claim 31 wherein the proximal end portion defines a sheath which is slidable axially in response to the activation of the shaft and is operably coupled to the distal end portion for allowing the axial movement of the distal end portion.

33. The system of claim 28 wherein the actuator includes at least one additional motor coupled to the stem for providing an axial force for moving the stem axially.

34. The system of claim 33 wherein the actuator is adapted to proximally withdraw the stem at a rate of 0.3 to 10 mm/sec.

35. The system of claim 24 further comprising a rotatable chuck member having a proximal end which is adapted to be in communication with the processor, the chuck member defining a lumen at least partially therethrough for receiving the proximal end portion of the stem.

36. The system of claim 35 further comprising an intervening connector having a first end and a second end with a length therebetween, wherein the first end is adapted for attachment to the proximal end of the chuck member and the second end is adapted to be in communication with the processor, and wherein the length is adapted to transmit a rotational movement to the stem.

37. The system of claim 24 further comprising an intervening connector having a first end and a second end with a length therebetween, wherein the first end is adapted for attachment to the proximal end portion of the stem and the second end is adapted to be in communication with the processor, and wherein the length is adapted to transmit a rotational movement to the stem.

38. The system of claim 24 further comprising a controller for controlling the rotational and axial movement of the stem, the controller being in electrical communication with the processor and the connector.

39. The system of claim 24 further comprising a pod which is adapted to be uniformly heated or cooled to a predetermined temperature for calibrating the system, the pod being further adapted to receive the detector during the calibration.

40. The system of claim 24 wherein the processor comprises a computer.

41. The system of claim 24 wherein the processor is in electrical communication with the connector.

42. The system of claim 24 wherein the processor is in optical communication with the connector.

43. The system of claim 24 further comprising a sensor mounted to the coil adjacent to the detector for measuring an impedance against the hollow body organ.

44. The system of claim 24 wherein the detector is adapted to have a measurement response time between about 10 to 100 msec.

45. The system of claim 24 wherein the detector is a type selected from the group consisting of thermocouples, thermistors, radiation sensors, oxygen sensors, ultrasonic transducers, impedance sensors, pH sensors, and mechanical force sensors.

* * * * *